(12) United States Patent
Autran et al.

(10) Patent No.: US 8,445,744 B2
(45) Date of Patent: *May 21, 2013

(54) EXTRUSION BONDED LAMINATES FOR ABSORBENT ARTICLES

(75) Inventors: Jean-Philippe Marie Autran, Wyoming, OH (US); Iyad Muslet, Mason, OH (US); David G. Bland, Mason, OH (US); Leopoldo V. Cancio, Vero Beach, FL (US); Janet Neton, West Chester, OH (US); Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 780 days.

This patent is subject to a terminal disclaimer.

(21) Appl. No.: 12/507,434

(22) Filed: Jul. 22, 2009

(65) Prior Publication Data

US 2010/0040826 A1 Feb. 18, 2010

Related U.S. Application Data

(63) Continuation-in-part of application No. 12/358,962, filed on Jan. 23, 2009, now Pat. No. 8,168,853.

(60) Provisional application No. 61/023,107, filed on Jan. 24, 2008.

(51) Int. Cl.
*A61F 13/514* (2006.01)
*B32B 27/12* (2006.01)

(52) U.S. Cl.
USPC .......................................... 604/365; 442/398

(58) Field of Classification Search
USPC ..................... 604/365, 367, 385.23; 442/364, 442/398
See application file for complete search history.

(56) References Cited

U.S. PATENT DOCUMENTS 3,692,618 A 9/1972 Dorschner et al.
3,802,817 A 4/1974 Matsuki et al.
(Continued)

FOREIGN PATENT DOCUMENTS

EP 1256594 11/2002
WO WO 03/039420 5/2003
(Continued)

OTHER PUBLICATIONS

International Search Report PCT/US2009/051392 dated Nov. 13, 2009.

*Primary Examiner* — Melanie Hand
*Assistant Examiner* — Paula Craig
(74) *Attorney, Agent, or Firm* — Kathleen Y. Carter; Richard L. Alexander

(57) ABSTRACT

An absorbent article of the present invention may comprise a topsheet, an outer cover, and an absorbent core disposed therebetween. The outer cover may comprise an extrusion bonded laminate. The EBL may comprise a multi-layer coextruded elastomeric film and a nonwoven. The film may comprise a core layer, a first outer layer, and a second outer layer, wherein the core layer is between the first and second outer layers. The nonwoven may comprise fibers and/or filaments. The first outer layer may be non-adhesively joined to the nonwoven via extrusion coating. Further, the outer cover may be elastic to at least about 50% engineering strain. The nonwoven may have high chemical affinity for the first outer layer. The first outer layer may have a low chemical affinity for the core layer. And, the first outer layer may comprise an amount of draw down polymer greater than about 45 wt %.

18 Claims, 5 Drawing Sheets

U.S. PATENT DOCUMENTS

| | | | |
|---|---|---|---|
| 3,855,046 A | 12/1974 | Hansen et al. | |
| 3,860,003 A | 1/1975 | Buell | |
| 4,021,284 A | 5/1977 | Kalwaites | |
| 4,024,612 A | 5/1977 | Contractor et al. | |
| 4,116,892 A | 9/1978 | Schwarz | |
| 4,340,563 A | 7/1982 | Appel et al. | |
| 4,515,595 A | 5/1985 | Kievit et al. | |
| 4,834,741 A | 5/1989 | Sabee | |
| 4,888,231 A | 12/1989 | Angstadt | |
| 4,940,464 A | 7/1990 | Van Gompel et al. | |
| 5,092,861 A | 3/1992 | Nomura et al. | |
| 5,143,679 A | 9/1992 | Weber et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 5,246,433 A | 9/1993 | Hasse et al. | |
| 5,366,782 A | 11/1994 | Curro et al. | |
| 5,422,172 A | 6/1995 | Wu | |
| 5,518,801 A | 5/1996 | Chappell et al. | |
| 5,569,234 A | 10/1996 | Buell et al. | |
| 5,691,035 A | 11/1997 | Chappell et al. | |
| 5,807,368 A * | 9/1998 | Helmer | 604/373 |
| 5,897,545 A | 4/1999 | Kline et al. | |
| 5,932,497 A | 8/1999 | Morman et al. | |
| 5,957,908 A | 9/1999 | Kline et al. | |
| 6,013,151 A | 1/2000 | Wu et al. | |
| 6,013,589 A | 1/2000 | DesMarais et al. | |
| 6,120,487 A | 9/2000 | Ashton | |
| 6,120,489 A | 9/2000 | Johnson et al. | |
| 6,169,151 B1 | 1/2001 | Waymouth et al. | |
| 6,342,565 B1 | 1/2002 | Cheng et al. | |
| 6,500,563 B1 | 12/2002 | Datta et al. | |
| 6,518,378 B2 | 2/2003 | Waymouth et al. | |
| 6,531,027 B1 | 3/2003 | Lender et al. | |
| 6,555,643 B1 | 4/2003 | Rieger | |
| 6,559,262 B1 | 5/2003 | Waymouth et al. | |
| 7,056,411 B2 | 6/2006 | Desai et al. | |
| 8,168,853 B2 * | 5/2012 | Autran et al. | 604/365 |
| 8,198,200 B2 * | 6/2012 | Autran et al. | 442/328 |
| 2003/0088228 A1 | 5/2003 | Desai et al. | |
| 2003/0225382 A1 | 12/2003 | Tombult-Meyer et al. | |
| 2003/0233082 A1 | 12/2003 | Kline et al. | |
| 2004/0091693 A1 * | 5/2004 | Thomas et al. | 428/317.9 |
| 2004/0193133 A1 | 9/2004 | Desai et al. | |
| 2004/0222553 A1 | 11/2004 | Desai et al. | |
| 2005/0070866 A1 | 3/2005 | Isele et al. | |
| 2005/0214461 A1 | 9/2005 | Desai et al. | |
| 2005/0215963 A1 | 9/2005 | Autran et al. | |
| 2005/0215964 A1 | 9/2005 | Autran et al. | |
| 2005/0287892 A1 | 12/2005 | Fouse et al. | |
| 2006/0014460 A1 | 1/2006 | Alexander Isele et al. | |
| 2006/0084342 A1 * | 4/2006 | Austin et al. | 442/361 |
| 2006/0155253 A1 | 7/2006 | Dziezok et al. | |
| 2006/0155254 A1 | 7/2006 | Sanz et al. | |
| 2006/0251858 A1 * | 11/2006 | Thomas et al. | 428/138 |
| 2007/0003764 A1 * | 1/2007 | Muslet et al. | 428/411.1 |
| 2007/0049888 A1 * | 3/2007 | Soerens et al. | 604/372 |
| 2007/0287348 A1 | 12/2007 | Autran et al. | |
| 2008/0003911 A1 | 1/2008 | Sabbagh et al. | |
| 2008/0045917 A1 | 2/2008 | Autran et al. | |
| 2009/0054861 A1 * | 2/2009 | Watson et al. | 604/365 |
| 2012/0184169 A1 * | 7/2012 | Autran et al. | 442/381 |

FOREIGN PATENT DOCUMENTS

| | | |
|---|---|---|
| WO | WO 03/053308 | 7/2003 |
| WO | WO 2005/073308 | 8/2005 |
| WO | WO 2005/073309 | 8/2005 |
| WO | WO 2005/097358 | 10/2005 |
| WO | WO 2005/097512 | 10/2005 |
| WO | WO 2007/146149 | 12/2007 |
| WO | WO 2007146148 A2 * | 12/2007 |

* cited by examiner

EXTRUSION BONDED LAMINATES FOR ABSORBENT ARTICLES

CROSS REFERENCE TO RELATED APPLICATIONS

This application is a continuation-in-part of U.S. patent application Ser. No. 12/358,962, filed Jan. 23, 2009, now U.S. Pat. No. 8,168,853, which claims the benefit of U.S. Provisional Application No. 61/023,107, filed Jan. 24, 2008, both of which are incorporated herein by reference.

FIELD OF THE INVENTION

The present invention generally relates to laminates useful for incorporation into absorbent articles. More specifically, the present invention relates to the materials and methods for making various elastomeric extrusion bonded laminates and their incorporation into a diaper.

BACKGROUND OF THE INVENTION

Absorbent articles such as conventional taped diapers, pull-on diapers, training pants, incontinence briefs, and the like, offer the benefit of receiving and containing urine and/or other bodily exudates. Such absorbent articles can include a chassis that defines a waist opening and a pair of leg openings.

Conventional chassis often include substantially inelastic outer covers. In order to provide for some stretch properties, conventional outer covers can include elastomeric waistbands and elastomeric leg bands surrounding a portion of the leg openings (e.g., barrier leg cuffs). The remainder of the outer cover typically includes a non-elastomeric nonwoven-film laminate. Undesirably, however, due to these non-elastomeric laminates, these articles offer limited conformity to a wearer's body in response to body movements (e.g. sitting, standing, and walking), due to the relative anatomic dimensional changes (which can, in some instances, be up to 50%) in the buttocks and abdominal region caused by these movements. This conformity problem is further exacerbated because one diaper typically must fit many wearers of various shapes and sizes in a single product size.

The challenge of conformity further resides in the fact that the dimensions of the smallest and biggest wearers within a given product size range can be markedly different. For instance, in the case of wearers, the waist circumference at the navel can vary by 80 mm within a size range. Also, the navel-to-back distance, which is the distance from the navel, around the crotch, and to a point on the back of the wearer that is in the same horizontal plane as the navel, can vary by about 80 mm from the smallest to the largest wearers in this same size range.

One solution to the above-stated problems is to provide elastomeric nonwoven-film laminate (e.g., some combination of a nonwoven with an elastomeric film) that may be used as an outer cover. But providing such a laminate is no trivial task, especially if one attempts to do so economically. First, for the sake of process simplicity and cost efficiency, there is a desire to use a minimum of processing or handling steps to produce the laminate. Thus, different surfaces or layers of an elastomeric film, having the same chemical and physical properties, may need to perform more than one function (e.g., a film layer that functions as a tie layer, as well as a skin layer), or may require certain properties during manufacture of an extrusion bonded laminate (EBL), different properties during absorbent article converting, and still different properties when the absorbent article is used by the consumer.

Second, there are several desirable embodiments that require the combination of laminate layers having a low chemical affinity for each other (e.g., the combination of an inelastic nonwoven and an elastomeric film). Increasing the penetration of the extrudate into a nonwoven structure may improve the bonding between these two materials, but this can result in a composite structure that is unpleasantly stiff and may be difficult to activate without damaging the resulting EBL. Thus, a tie layer or an adhesive may need to be employed in order to produce a laminate that can be produced at a reasonable rate, resists separation during subsequent processing, and maintains a suitable drape or hand. If a tie layer is employed (which has advantages over an adhesive, including process simplicity), one needs to not only balance bond strength between the tie layer and the nonwoven, but also the interaction between the tie layer and the core layer. For instance, if the bond strength to the nonwoven is too high, activation of the laminate becomes difficult. If, however, the bond strength is too weak, the laminate is subject to delamination. Third, striking the right balance in bond strength is further complicated by the need to achieve a laminate having particular extension, recovery, set and tensile properties.

Fourth, because laminates are often manufactured at a site different from the location where the laminate will be converted into a finished absorbent article, there may be a need to build a base laminate that includes a skin layer that may enable the base laminate to be wound and unwound after prolonged storage conditions without blocking.

Fifth, it may be desirable to select an activatable nonwoven, a tie layer, or the combination of both that can dissipate energy and avoid unwanted concentration of stresses in the film during mechanical activation of the laminate. That is, when using an inelastic nonwoven in combination with an elastic film, the need to activate the laminate will exist. Activation is, however, demanding for the elastic film, and can cause damage to the laminate film (e.g., formation of unwanted holes in the film), thus creating undesirable laminate properties. Therefore, use of a tie layer may offer the additional advantage of dissipating the energy of the activation process such that the integrity of the elastic film and appearance of the nonwoven is better maintained (i.e., a tie layer that acts as a buffer).

Thus, it is an object of the present invention to provide an elastomeric nonwoven-film laminate with good tensile properties. It is a further object of the invention to provide such a laminate comprising one or more tie layers, the laminate being capable of being mechanically activated without delamination. Another object of the invention is to provide an elastomeric nonwoven-film laminate as described using no more than two extruders. Still further, it is an object of the present invention to provide an elastomeric nonwoven-film laminate capable of being wound, stored, and unwound within acceptable parameters. Finally, it is an object of the present invention to provide an elastomeric nonwoven-film laminate comprising a tie layer that acts as a buffer to enable pinhole-free mechanical activation.

SUMMARY OF THE INVENTION

An absorbent article of the present invention may comprise a topsheet, an outer cover, and an absorbent core disposed therebetween. The outer cover may comprise an extrusion bonded laminate. The EBL may comprise a multi-layer coextruded elastomeric film and a nonwoven. The film may comprise a core layer, a first outer layer, and a second outer layer, wherein the core layer is between the first and second outer layers. The nonwoven may comprise fibers and/or filaments.

The first outer layer may be non-adhesively joined to the nonwoven via extrusion coating. And, the first outer layer may comprise an amount of draw down polymer greater than about 45 wt %.

Further, the outer cover may be elastic to at least about 50% engineering strain. The nonwoven may have high chemical affinity for the first outer layer. The first outer layer may have a low chemical affinity for the core layer.

The extrusion bonded laminate may be activated. The first and second outer layers may have a fusion index from about 10% to about 40%. The first and second outer layers may be selected from the group consisting of ethylene copolymer, propylene copolymer, and mixtures thereof.

The nonwoven may be activatable and may be selected from the group consisting of polypropylene, polyethylene, and combinations thereof.

The nonwoven may comprise bicomponent fibers, the fibers comprising a core and a sheath. The sheath may comprise polyethylene and the core comprises polypropylene. The polyethylene may have a fusion index from about 50% to about 75%. The polypropylene may have a fusion index greater than about 50%.

The core of the elastomeric film may be selected from the group consisting of ethylene copolymer, propylene copolymer, styrenic block copolymers, and mixtures thereof. The core of the elastomeric film may be selected from the group consisting of an ethylene copolymer having a fusion index from about 5% to about 20%, a propylene copolymer having a fusion index from about 5% to about 20%, and combinations thereof. The first and second outer layers may each have a fusion index greater than the overall fusion index of the core layer.

The EBL may have a basis weight from about 30 to about 70 gsm and may further comprise an adhesive. The nonwoven may comprise fibers that are not round in cross section. The first outer layer may comprise at least about 25% of a polymer comprising more than 10 w % ethylene.

Alternatively, the nonwoven may be an activatable polypropylene monofilament, and the first outer layer may comprise at least about 25% of a polymer comprising more than 10 w % ethylene.

A second nonwoven may be joined to the second outer layer, wherein the second nonwoven is different than the nonwoven joined to the first outer layer. Each of the nonwovens may be selected from the group consisting of spunbond nonwoven webs, carded nonwoven webs, meltblown nonwoven webs, and spunlaced nonwoven webs, spunbond meltblown spunbond, spunbond meltblown meltblown spunbond, unbonded nonwoven, and combinations thereof.

When the EBL is activated, the laminate bond strength may be from about 1.0 to about 1.5 N/cm or from about 2.1 to about 3.5 N/cm, as measured by the Tensile Test (Mode II).

An exterior surface of the second outer layer may have a blocking force of less than 0.4 N/cm. The EBL may be adhesive free. The elastomeric film may have a basis weight from about 20 to about 40 gsm. The elastomeric film may comprise at least about 50%, by weight, of a polyolefinic elastomer.

Further, the elastomeric film may comprise at least one olefin-based elastomeric polymer and at least one draw down polymer, wherein the elastomeric film has a permanent set of no more than about 15% as measured by the Two-Cycle Hysteresis Test Method using 100% maximum engineering strain. More particularly, the first and second outer layers of the elastomeric film may comprise at least one olefin-based elastomeric polymer and at least one first draw down polymer; and the core layer of the elastomeric film may comprise at least one elastomeric polymer and at least one second draw down polymer, wherein the elastomeric film has a permanent set of no more than about 15% as measured by the Two-Cycle Hysteresis Test Method using 100% maximum engineering strain.

At least one elastomeric polymer of the core layer may not be an olefin-based elastomeric polymer. The first and second outer layers may be compositionally identical. The outer cover may have an ultimate tensile strength of greater than about 3 N/cm.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Definitions

As used herein, the following terms shall have the meaning specified thereafter:

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a preformed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

Figure 4:
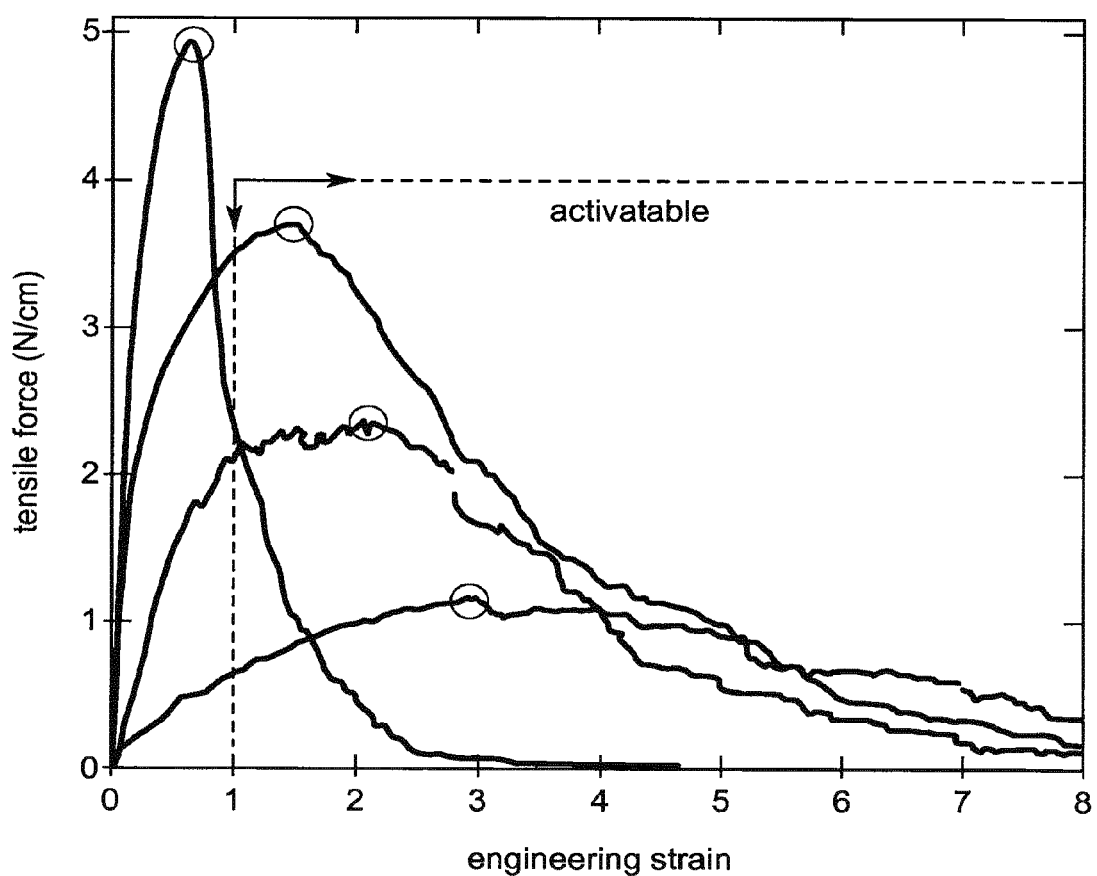
FIG. 4 is a graph illustrating tensile properties of activatable nonwovens (three shown) useful in absorbent articles of the present invention versus a non-activatable nonwoven (one shown).

"Activatable nonwoven" refers specifically to nonwovens that have mechanical properties that interact well with films during the activation process. Activatable nonwovens of the present invention give tensile curves (ASTM D882-02, gauge length=5 mm, specimen width=25.4 mm, crosshead speed=2.117 mm/s, deformation direction coinciding with that applied during the activation process) characterized by relatively low maximum forces and relatively large engineering strains. Specifically, if the nonwoven's curve's maximum force point lies below 4 N/cm at an engineering strain value of greater than 100%, then, for the purposes of the present invention, it is deemed to be "activatable." Examples of three activatable nonwovens and one non-activatable nonwoven are shown in FIG. 4. In FIG. 4, each curve's maximum force point is encircled.

"Activated" refers to a material which has been mechanically deformed so as to impart elasticity to at least a portion of the material, such as, for example by incremental stretching. U.S. Pat. Nos. 6,830,800, 5,143,679, and 5,167,897 disclose examples of the activation process.

"Adhesive" refers to compositions comprising one or more thermoplastic polymers, one or more tackifier resins, and typically a rheology modifier or plasticizer. Adhesives contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

"Adhesive-free" refers to a laminate where an adhesive is not used to bond the elastomeric member (e.g., elastomeric film) to the nonwoven or nonwovens, and therefore an adhesive is not part of the final laminate structure.

"Adhesively bonded" or "adhesively laminated" refers to a laminate wherein an adhesive is used to bond an elastomeric member (e.g., elastomeric film) to a nonwoven(s).

"Bicomponent fiber" refers to fibers or filaments consisting of material of two different compositions arranged across the cross-section of the fiber or filament. Each composition is typically delivered by a separate extruder to a spin pack designed to arrange the compositions into arrangements such as sheath-core, side-by-side, segmented pie and islands-in-the-sea. The mutual arrangement of different compositions can be beneficial in tailoring the chemical affinity between a film and a nonwoven in a laminate.

"Blocking" refers to the phenomenon of a film sticking to itself or to the opposite outer facing side of a composite laminate structure when the film or laminate is rolled, folded, or otherwise placed in intimate surface to surface contact.

"Body-facing," "inner-facing," "outer-facing," and "garment-facing" refer respectively to the relative location of an element or a surface of an element or group of elements. "Body-facing" and "inner-facing" imply the element or surface is nearer to the wearer's body during wear (i.e., closer to the wearer's body than a garment-facing surface or an outer-facing surface). "Garment-facing" and "outer-facing" imply the element or surface is more remote from the wearer during wear (i.e., element or surface is nearer to the wearer's garments that can be worn over the disposable absorbent article).

"Chemical affinity" refers to the nature of the chemical interaction between polymers. Two polymers are said to have a high degree of chemical affinity if their enthalpy of mixing is close to zero. Conversely, polymers with large enthalpies of mixing (and correspondingly large differences in solubility parameter) have little chemical affinity. (Solubility Parameters, section VII "Single-Value Solubility Parameters of Polymers", Polymer Handbook, 3rd Edition, 1989, J. Brandrup, E. H. Immergut, Ed. John Wiley & Sons, New York, Chichester, Brisbane, Toronto, Singapore). The following table shows the approximate values for the difference in solubility parameter values for a polymer pair to be considered have "low", "medium" or "high" chemical affinity:

| Degree of Chemical Affinity | Difference in Solubility Parameter (MPa$^{0.5}$) |
| --- | --- |
| low | 2.5 or greater |
| intermediate | 1.5-2.49 |
| high | 0-1.49 |

For example, polyethylene ("PE") at 16.0 MPa$^{0.5}$ and polypropylene ("PP") at 18.8 MPa$^{0.5}$ have a difference of 2.8 MPa$^{0.5}$ and therefore exhibit a low degree of chemical affinity. The method use to determine the solubility parameter of a polymer is described by Robert Hayes in the "Journal of Applied Polymer Science," volume 5, pages 318-321, 1961.

"Compositionally identical" refers to compositions that have such close resemblance as to be essentially the same (e.g., two layers of a multi-layer film having nominally the same ingredients in the same proportions (such as the A layers in an ABA co-extruded film)).

"Crystallization rate" refers to the kinetics of crystal nucleation and growth from a polymer melt, as it is cooled in, and following, an extrusion lamination process. Crystallization rate reflects the route by which a polymer solidifies from a molten, amorphous state. Differential Scanning Calorimetry (DSC) may be used according to ASTM D 3418 as described in more detail in the Test Methods to determine crystallization rates of polymers, polymer blends, and formulations comprising polymers useful in films, including skin and tie layers, of the present invention.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

"Disposed" refers to an element being positioned in a particular place with regard to another element. When one group of fibers is disposed on a second group of fibers, the first and second groups of fibers generally form a layered, laminate structure in which at least some fibers from the first and second groups are in contact with each other. In some embodiments, individual fibers from the first and/or second group at the interface between the two groups can be dispersed among the fibers of the adjacent group, thereby forming an at least partially intermingled, entangled fibrous region between the two groups. When a polymeric layer (for example a film), is disposed on a surface (for example a group or layer of fibers), the polymeric layer can be laminated to or printed on the surface.

"Elastic" and "elastomeric" are synonymous and refer to any material that upon application of a tensile force, can stretch to an elongated length of at least 10% engineering strain, without rupture or breakage. Further, upon release of the applied force, the material may recover at least 40% of its elongation within one minute at 22° C. For example, a material that has an initial length of 100 mm can extend at least to 110 mm, and upon removal of the force would retract to a length of 106 mm or less.

"Engineering strain" is the change in length of a specimen (in the direction of applied stress or strain) divided by the specimen's original length (William D. Callister Jr., "Materials Science and Engineering: An Introduction", 1985, John Wiley & Sons, Inc. New York, Chichester, Brisbane, Toronto, Singapore). To calculate percent engineering strain, the engineering strain is multiplied by 100.

"Ethylene rich" refers to the composition of a polymeric layer (e.g., a sheath of a bicomponent fiber or a skin layer of a film) or a portion of a layer of an EBL or nonwoven that comprises at least about 80% by weight of polyethylene (including homopolymers and copolymers). For example, a sheath of a core-sheath bicomponent fiber, wherein the sheath is comprised of greater than about 80% by weight of a linear, low density polyethylene, is ethylene rich.

"Extensible" refers to any material that upon application of a tensile force, can stretch to at least 10% engineering strain, without rupture or breakage. Further, upon release of the applied force, the material shows less than 40% recovery within one minute at a temperature of 22° C. For example, a material that has an initial length of 100 mm can extend to at least 110 mm, and upon removal of the force would retract to a length of greater than 106 mm.

"Extrusion bonded laminate ('EBL')" refers to a multilayer composite formed by extruding an elastomeric extrudate directly onto at least one nonwoven at or near a nip formed between two calender rollers, such that at least some nonwoven fibers penetrate into the soft extrudate film in order to join the film and the nonwoven. The amount of penetration of nonwoven into the soft extrudate may be controlled by selecting a nip gap smaller than the caliper of the nonwoven plus the film, by adjusting the pressure of the rolls, or by other means well understood to one of ordinary skill in the art. In one embodiment, the elastomeric extrudate may be a monolayer film comprising one or more elastomeric polymers. In another embodiment, the elastomeric extrudate may be a coextruded multilayer film with one or more outer layers comprising the same or different composition as a core layer of the film.

"Extrusion lamination" or "extrusion coating" refers to processes by which a film of molten polymer is extruded onto a solid substrate (e.g., a nonwoven), in order to coat the substrate with the molten polymer film to bond the substrate and film together.

"Joined" refers to configurations whereby an element is directly secured to another element by affixing the element directly to the other element and to configurations whereby an element is indirectly secured to another element by affixing the element to intermediate member(s) which in turn are affixed to the other element. Materials may be joined by one or more bonding processes including adhesive bonding, thermal welding, solvent welding, ultrasonic bonding, extrusion bonding, and combinations thereof.

"Liquid-permeable" (or "liquid-pervious") and "liquid-impermeable" (or "liquid-impervious") refer to the penetrability of materials in the context of the intended usage of disposable absorbent articles. Specifically, "liquid permeable" refers to a layer or a layered structure having pores, openings, and/or interconnected void spaces that permit liquid water to pass through its thickness at less than 5 mbar of hydrostatic head (as defined by INDA 80.6-01). Conversely, "liquid impermeable" refers to a layer or a layered structure through the thickness of which liquid water cannot pass through its thickness at less than 5 mbar of hydrostatic head (as defined by INDA 80.6-01). A layer or a layered structure that is water-impermeable according to this definition may be vapor-permeable, for example permitting transmission of air and water vapor. Such a vapor-permeable layer or layered structure is commonly known in the art as "breathable."

"Machine direction" (also "MD" or "length direction") as applied to a film or nonwoven material, refers to the direction that was parallel to the direction of travel of the film or nonwoven as it was processed in the forming apparatus. The "cross machine direction" (also "CD" or "width direction") refers to the direction perpendicular to the machine direction.

"Non-adhesively joined" refers to joining two or more materials without use of an adhesive. Non-limiting examples of non-adhesively joined materials include extrusion coating of a web, sonic welding of two or more webs, pressure bonding of at least one film and one or more nonwovens, etc.

"Outer cover" refers to that portion of the diaper which is disposed adjacent to the garment-facing surface of the absorbent core. Outer covers have tensile properties that enable ease of the application of the article, as well as enabling the article to conform to the wearer's body. In some embodiments it may prevent the excreta and/or exudates contained therein from soiling garments or other articles which may contact the diaper, such as bedsheets and clothing. In these embodiments, the outer cover may be impervious to liquids. In other embodiments, the outer cover may be liquid pervious. Outer covers of the present invention may comprise an EBL.

"Pant," "training pant," "pre-closed diaper," "pre-fastened diaper," "pull-on diaper," and "pant-like garment" as used herein, refer to disposable garments having a waist opening and leg openings designed for infant, children, or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

"Permanent set" is the permanent deformation of a material after removal of an applied load. In the case of elastomeric films, permanent set is the increase in length of a sample of a film after the film has been stretched to a given length and then allowed to relax as described in the Two Cycle Hysteresis Test. Permanent set is typically expressed as a percent increase relative to the original size.

"Propylene rich" refers to the composition of a polymeric layer (e.g., a sheath of a bicomponent fiber or a skin layer of a film) or a portion of a layer of an EBL or nonwoven that comprises at least about 80% by weight of polypropylene (including homopolymers and copolymers). For example, a tie layer comprising 96% VISTAMAXX 6102 (16% by weight PE/84% by weight PP), is propylene rich.

"Side panel," "front ear," "back ear," or "ear panel" refers to that portion of an absorbent article which is disposed adjacent to the outer cover or core or topsheet and connect a front waist edge to a back waist edge. Side panels or front/back ears have tensile properties that enable ease of the application of the article, as well as enabling the article to conform to the wearer's body. Side panels or front/back ears of the present invention may comprise an EBL. Examples of side panels that may be used in the present invention are described and illustrated in EP 1150833 (referenced as ear panels).

"Skin layer" refers to an outer layer of a coextruded, multilayer film that acts as an outer surface of the film during its production and subsequent processing.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

"Tie layer" refers to a layer of a coextruded, multilayer film that acts as an intermediary between a core layer of the film and another material, such that the laminate strength between the core layer and the other material is improved (increased or decreased). The tie layer's composition can be adjusted to modify or optimize the chemical and physical interactions between film and nonwoven. Tie layers of the present invention do not contain more than 2% of a tackifier resin, and are substantially continuous over the entire surface of the coextruded film. In the present invention, it may be desirable to have a tie layer and skin layer which are compositionally identical.

Figure 5A:
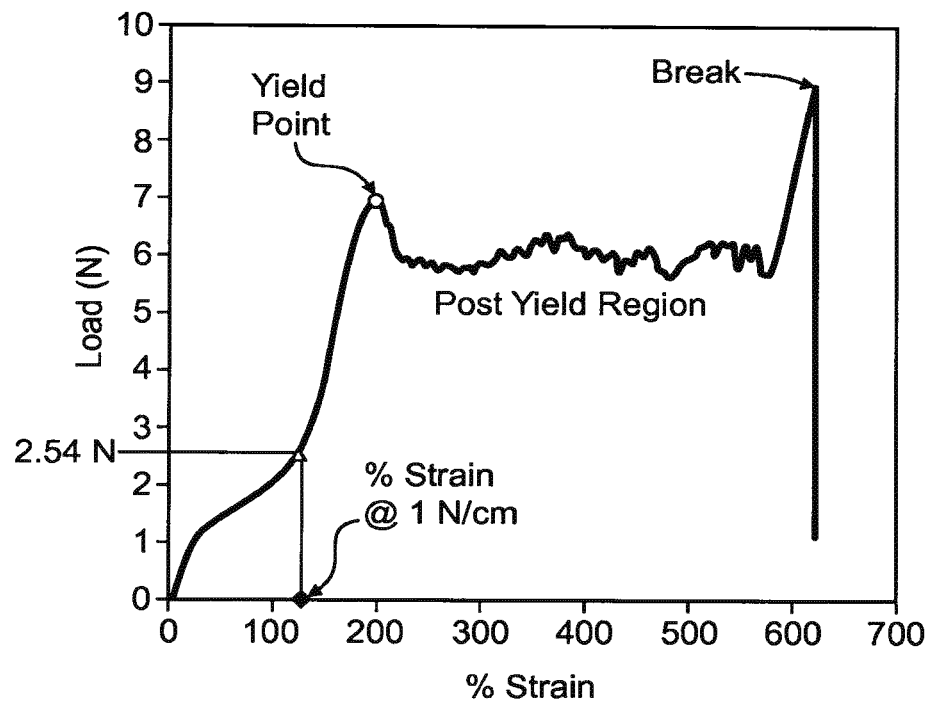
FIGS. 5A and 5B are graphs illustrating tensile properties of extrusion bonded laminates useful in absorbent articles of the present invention. From these graphs Mode II failure and peak force at break may be determined (see Test Methods).
Figure 5B:
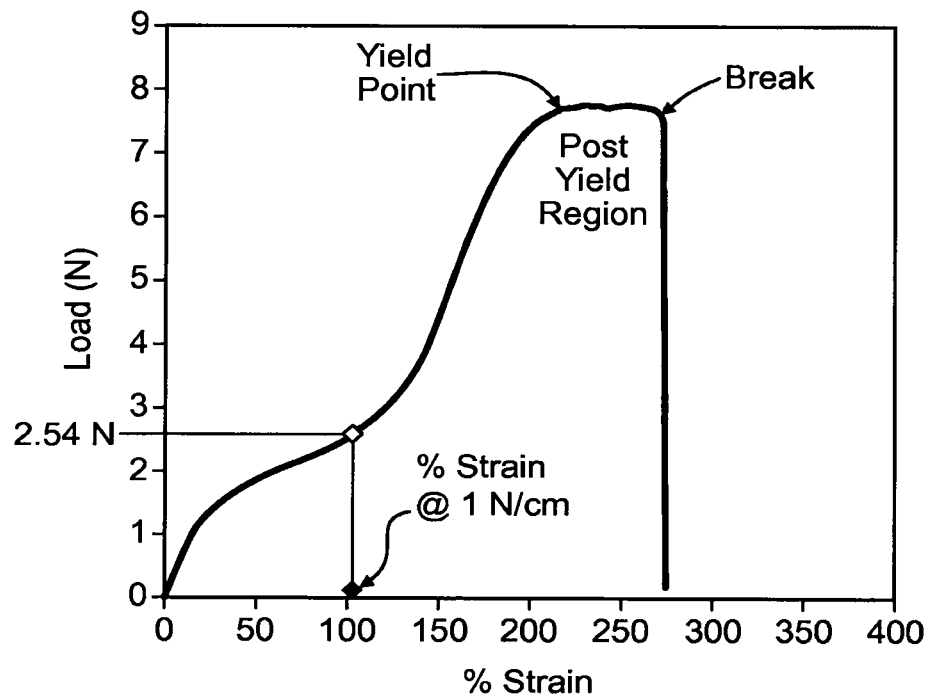

"Ultimate tensile strength" is the peak force and refers to the maximum value observed in N/cm (i.e., the peak force divided by the sample width, for example, at the "break" in FIG. 5A and at the "yield point" in FIG. 5B).

General Description of the Laminates of the Present Invention

Figure 1:
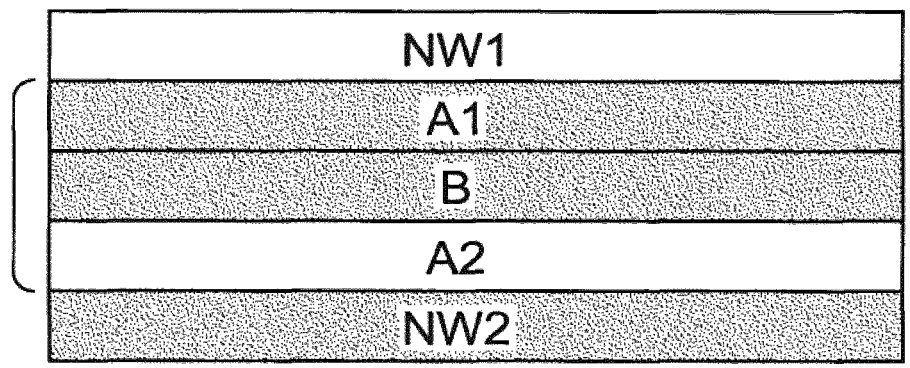
FIGS. 1, 6A, 6B, 6C, 7, and 8 are sectional side views of an EBL useful in absorbent articles of the present invention.
Figure 6A:
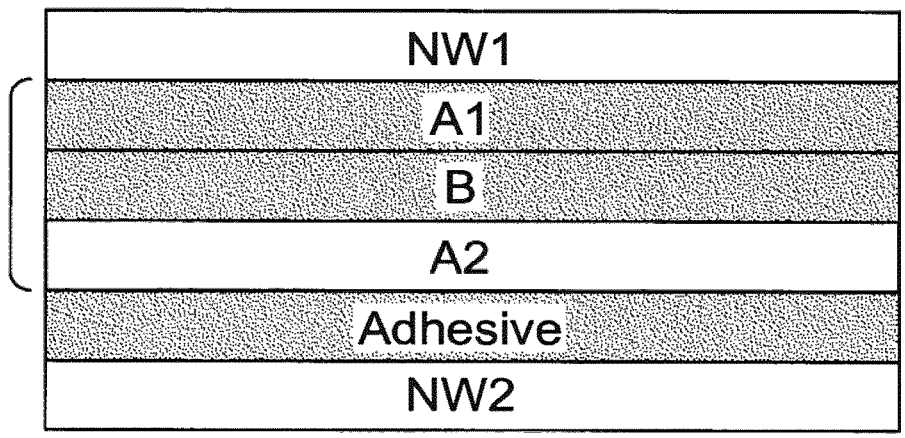
Figure 6B:
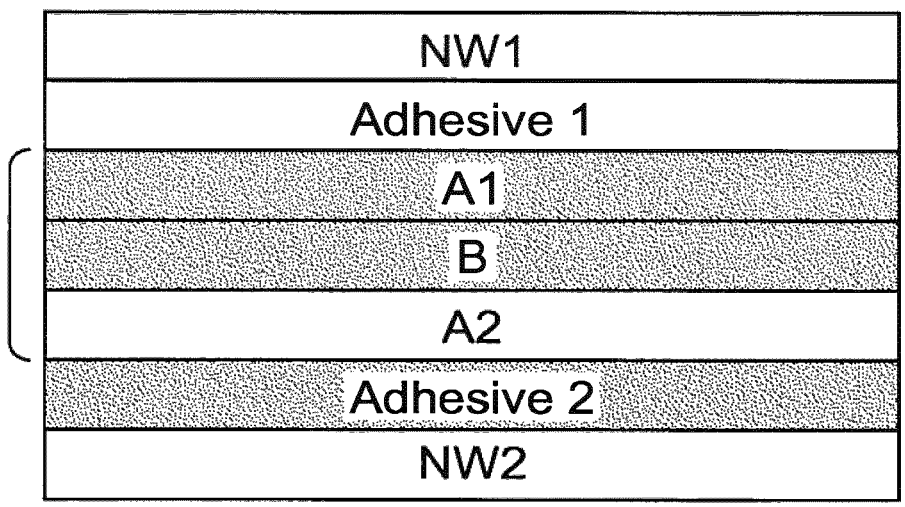
Figure 6C:
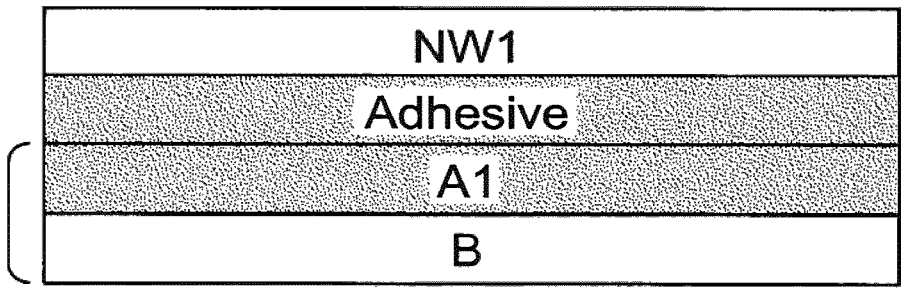
Figure 7:
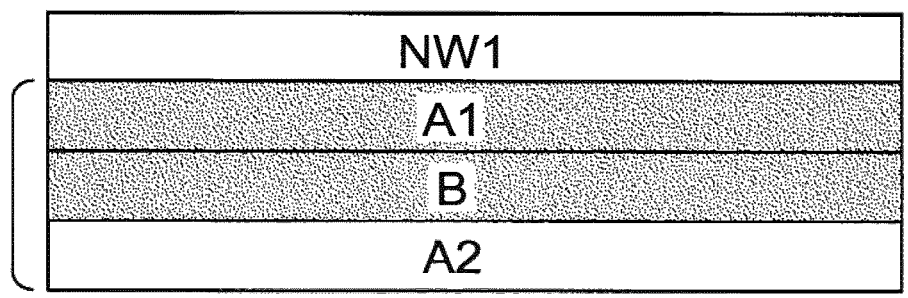
Figure 8:
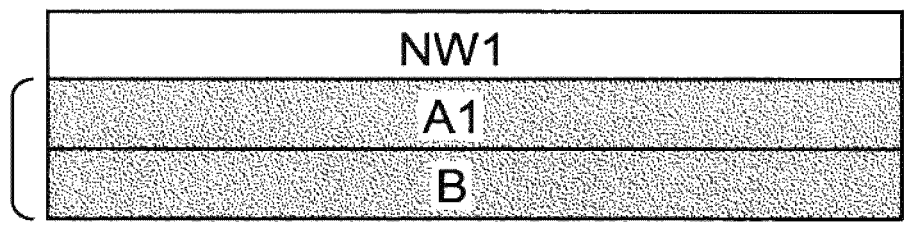

Referring to FIG. 1, EBLs of the present invention may include at least one nonwoven (NW1) (which may have multiple layers, e.g., SMS, SSMMS, etc.) joined to an elastomeric film (which may comprise multiple film layers (e.g., A1, B, and A2)). The elastomeric film of the present invention may comprise at least one tie layer (A1), and at least one core layer (B). In certain embodiments, laminates useful in absorbent article of the present invention may comprise a skin layer (A2), which may be compositionally identical to the tie layer. Further embodiments of the present invention may comprise two nonwovens (such that (1) a first nonwoven (NW1) is joined to the EBL via a first tie layer (A1) and a second nonwoven (NW2) is joined to the EBL via a second tie layer (A2) or (2) such that a first nonwoven (NW1) is joined to the EBL via a tie layer (A1) and a second nonwoven (NW2) is joined to the EBL via an adhesive). Still further, as shown in FIGS. 6A, 6B, and 6C, embodiments of the present invention may include a nonwoven joined to a film via a tie layer in combination with one or more adhesives (which may be referred to as "adhesive assist"). Adhesives 1 and 2 may be compositionally identical or may different. Further, adhesives 1 and 2 may be applied by the same or different means (e.g., adhesive 1 may be slot coated while adhesive 2 may be sprayed). FIGS. 7 and 8 illustrate additional embodiments of the EBLs useful in absorbent articles of the present as described above.

Elastomeric Films of the Present Invention

One or more layers of the elastomeric film (illustrated as layers A1, B, and A2 in FIG. 1) may provide the desired amount of extension and recovery forces during use of the laminate. As mentioned above, the elastomeric film may comprise one or more film layers. Many suitable elastic materials that may be used for one or more layers of the elastomeric film include synthetic or natural rubbers (e.g., crosslinked polyisoprene, polybutadiene and their saturated versions (after hydrogenation), and polyisobutylene), thermoplastic elastomers based on multi-block copolymers, such as those comprising copolymerized rubber elastomeric blocks with polystyrene blocks (e.g., styrene-isoprene-styrene, styrene-butadiene-styrene, styrene-ethylene/butylene-styrene, styrene-ethylene/propylene-styrene, and styrene-butadiene/isoprene-styrene, including their hydrogenated and non-hydrogenated forms), thermoplastic elastomers based on polyurethanes, polyesters, polyether amides, elastomeric polyolefins including polyethylenes and polypropylenes, elastomeric polyolefin blends, and combinations thereof.

For instance, one useful group of elastomeric polymers that may be used in the elastomeric film are the block copolymers of vinyl arylene and conjugated diene monomers, such as AB, ABA, ABC, or ABCA block copolymers where the A segments may comprise arylenes such as polystyrene and the B and C segments (for those embodiments comprising B and/or C segments) may comprise dienes such as butadiene or isoprene. A similar, newer group of elastomeric polymers are the block copolymers of vinyl arylene and hydrogenated olefin monomers, such as AB, ABA, ABC, or ABCA block copolymers where the A segments may comprise arylenes such as polystyrene and the B and C segments (for those embodiments comprising B and/or C segments) may comprise saturated olefins such as ethylene, propylene, or butylene. Suitable block copolymer resins are readily available from KRATON® Polymers of Houston, Tex., Dexco™ Polymers LP of Planquemine, La., or Septon™ Company of America, Pasadena, Tex.

Another useful group of elastomeric polymers that may be used in the elastomeric film are olefin-based elastomers. In one embodiment, the elastomeric film comprises a polyolefinic elastomer (POE). Examples of POEs include olefin block copolymers (OBCs) which are elastomeric copolymers of polyethylene, sold under the trade name INFUSE™ by The Dow Chemical Company of Midland, Mich. Other examples of POEs include copolymers of polypropylene and polyethylene, sold under the trade name VISTAMAXX® by ExxonMobil Chemical Company of Houston, Tex. and/or VERSIFY by Dow Chemical, Midland, Mich.

For the elastomeric film, other polymers may be blended into the compositions to enhance desired properties. For example, a linear low-density polyethylene may be added to the film composition to lower the viscosity of the polymer melt and enhance the processability of the extruded film. High-density polyethylene may be added to prevent age-related degradation of the other polymers. Polypropylene has been found to improve the robustness of the elastomer and improve the films' resistance to pinholing and tearing. Additionally, polypropylene-based thermoplastic elastomer reactor blends (e.g., ADFLEX, available from LyondellBasell Industries, Laporte, Tex.) may be used to increase the toughness the film, as disclosed in WO 2007/146149.

Regarding elastomeric polypropylenes, in these materials propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518, 378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher alpha-olefin) incorporated into the backbone. Suitable elastomeric RCP materials are available under the names VISTAMAXX and VERSIFY as mentioned above.

In another embodiment, the inventive elastomeric film may comprise multiple layers. Further, the elastomeric film may comprise a coextruded multilayer film with an ABA-type construction. The two A layers may comprise the same composition, and form the outer layers of the film, which may also be referred to as the 'skin,' 'surface,' or 'tie' layers. In the present invention, the skin layer may be compositionally identical to the tie layer. The B layer, which forms the 'core' or 'central' layer, may be compositionally identical to the A layers, or the B layer may comprise a composition other than the A layers. Each layer of a multilayer elastomeric film may comprise elastomeric polymers, or the layers may comprise either elastomeric or thermoplastic non-elastomeric polymers, either singly or in combination, in each layer.

For the embodiment in which the elastomeric film is a multilayer film of ABA construction, the A layers, which are the skin or tie layers, may comprise an elastomeric polymer. For the A layers, the use of polyolefin-based elastomers may be desired. It has been unexpectedly discovered that A layers comprising POEs improve the processability of the elastomeric film, as discussed above, even when the core layer is a styrene block copolymer (SBC) or other less-processable polymer. Also as discussed above, POEs on the surface of the film may have a greater chemical affinity for a polyolefinic fabric joined to the surface of the film in the laminate. This greater chemical affinity may improve the laminate strength between the film surface and a nonwoven.

For the B layer or core of the multilayer ABA elastomeric film, the core may comprise any elastomeric polymer. In one embodiment, the core layer may be an SBC, such as styrene-butadiene-styrene (SBS), styrene-isoprene-styrene (SIS), styrene-ethylenebutadiene-styrene (SEBS), styrene-ethylene-propylene (SEP), styrene-ethylene-propylene-styrene (SEPS), or styrene-ethylene-ethylene-propylene-styrene (SEEPS) block copolymer elastomers, or blends thereof. SBC elastomers exhibit superior elastomeric properties. The presence of SBC elastomers in the core layer of the multilayer elastomeric film yields a film that has excellent stretch and recovery characteristics. As discussed previously, however, unsaturated SBC elastomers are prone to thermal degradation when they are overheated, and saturated SBC's tend to be very expensive. Additionally, SBC's can be difficult to process and extrude into films, especially thin films of the present invention. In another embodiment, the B layer, or core layer of the multilayer film, may be a thermoplastic polyolefin, such as the elastomeric polypropylenes mentioned above, the olefin block copolymers of predominantly ethylene monomers mentioned above, the polypropylene-based thermoplastic elastomer reactor blends mentioned above, and combinations thereof.

In addition to the elastomeric polymer in the core layer, other polymeric components may be added to the core layer composition to improve the properties of the film. For example, a linear low-density polyethylene may be added to the film composition to lower the viscosity of the polymer melt and enhance the processability of the extruded film. High-density polyethylene may be added to prevent age-related degradation of the other polymers. High-impact polystyrene (HIPS) has been found to control the film modulus, improve the toughness of the film, and reduce the overall cost of the elastomeric material.

In the present invention, homopolymer polypropylene (hPP) may be blended into the core layer composition to improve processability. hPP is a form of polypropylene which is highly crystalline and containing essentially 100% propylene monomer. It has been found that SBC-based elastomeric films with hPP can be extruded at a thinner gauge and with improved gauge uniformity, and the addition of hPP may reduce the tendency of the film to experience draw resonance during extrusion.

The elastomeric film of the present invention may optionally comprise other components to modify the film properties, aid in the processing of the film, or modify the appearance of the film. Viscosity-reducing polymers and plasticizers may be added as processing aids. Other additives such as pigments, dyes, antioxidants, antistatic agents, slip agents, foaming agents, heat and/or light stabilizers, and inorganic and/or organic fillers may be added. These additives may optionally be present in one, several, or all layers of a multilayer elastomeric film.

In order to manufacture a thin-gauge elastomeric film, the average basis weight of the elastomeric film may be controlled. If a polymer is hard to process, then the extruded film of that polymer will likely be hard to control. This lack of control is seen in problems like fluctuating basis weights, draw resonance, web tear-offs, and other significant problems. As discussed above, SBC elastomers tend to have relatively poor processability, and hence it is very hard to manufacture a film with a controlled basis weight. These problems are only magnified as one attempts to manufacture a film with a lower basis weight.

However, by extruding films comprising POE polymers or, alternatively, POE polymer outer layers (e.g., tie or skin layers), the processability of the elastomeric film is improved, and the problems associated with basis weight control are reduced or eliminated. The inventors have discovered that thin-gauge films are much easier to manufacture, even with high concentrations of SBCs in the core layer, when the outer layers comprise POE polymers.

Another problem with manufacturing lower basis-weight films is their reduced mass, which causes the extruded polymer web to solidify more rapidly. If the extruded polymer web solidifies too quickly, then the polymer film is 'locked' into the thickness that exists at that time. This situation is directly comparable to the 'frost line' experienced in blown film technology. Once the film has solidified, it cannot be easily drawn to a thinner gauge. This is particularly a problem with elastomers like unsaturated SBCs, which are prone to thermal degradation when heated to excessively high temperatures. Simply heating the unsaturated SBC to a higher temperature to compensate for the reduced mass of the extruded web may not be sufficient.

POE elastomeric polymers, however, are more thermally stable than SBC elastomers, and thus, can be heated to a higher temperature without degradation. This increases the total heat present in the extruded polymer web, so the web releases more heat before solidifying. POEs also solidify at lower temperatures than do SBCs, so there is a greater differential between the temperature of the extruded polymer and the temperature at which the film solidifies. The inventors have also discovered, unexpectedly, that coextruding an SBC-based core within POE-based outer layers both allows the coextruded multilayer film to be extruded at a higher overall temperature, thereby compensating somewhat for the reduced-mass heat loss, and also increases the time it takes for the molten extrudate to solidify. This allows the manufacturer to extrude the multilayer elastomeric polymer film and draw it to a lower basis weight before the film solidifies.

It may be desirable for certain aspects of the present invention to use an elastic film that is less than about 65 gsm or less than about 30 gsm or less than 20 gsm, but greater than about 1 gsm, about 5 gsm, or about 10 gsm. The approximate basis weights of the films may be measured according to the commonly understood method referred to as "mass balance." Further, thicknesses of the films may be determined using SEM or optical microscopy.

Elastic films of the present invention may have a thickness or a caliper (which may be referred to as the z-direction thickness) in the range from about 1 μm to about 65 μm (which corresponds from about 0.9 to about 65 gsm), from about 5 μm to about 30 μm (which corresponds from about 4 to about 30 gsm), from about 10 μm to about 20 μm (which corresponds from about 9 to about 20 gsm), and from about 12 μm to about 17 μm (which corresponds from about 10 to about 17 gsm).

Nonwovens of the Present Invention

The inventive elastomeric film may be combined with a nonwoven. The nonwovens (illustrated as NW1 and NW2 in FIG. 1) may be activatable sheet-like materials, such as fabrics. The nonwoven of the present invention is generally formed from fibers which are interlaid in an irregular fashion using such processes as meltblowing, air laying, coforming, and carding. In some embodiments, the nonwoven may include spunbond fibers in a single layer (S) or multiple layers (SSS). In other embodiments, fibers of different diameters or compositions may be blended together in a single layer, or fibers of different diameters or compositions may be present in multiple layers, as in spunbond-meltblown-spunbond (SMS) constructions and spunbond-spunbond-meltblown-meltblown-spunbond (SSMMS) constructions. The fibers of the nonwoven material may be joined together using conventional techniques, such as thermal point bonding, ultrasonic point bonding, adhesive pattern bonding, and adhesive spray bonding. Examples of activatable nonwovens useful in the present invention include those described in U.S. Pat. No. 6,417,121.

These fabrics may comprise fibers of polyolefins such as polypropylene or polyethylene, polyesters, polyamides, polyurethanes, elastomers, rayon, cellulose, copolymers thereof, or blends thereof or mixtures thereof. For a detailed description of nonwovens, see "Nonwoven Fabric Primer and Reference Sampler" by E. A. Vaughn, Association of the Nonwoven Fabrics Industry, 3d Edition (1992).

One or more components or layers of the nonwoven may comprise bicomponent fibers. The bicomponent fiber may be of any suitable configuration. Exemplary configurations include but are not limited to sheath-core, island-in-the-sea, side-by-side, segmented pie and combinations thereof (as disclosed in U.S. Pat. No. 5,405,682). In one optional embodiment of the present invention the bicomponent fibers have a sheath-core configuration. The sheath may be predominately comprised of polyethylene and the core may be predominately comprised of polypropylene. These fibers may have a diameter or equivalent diameter of from about 0.5 micron to about 200 microns or from about 10 and to about 40 microns.

Typically, the bicomponent fibers described above are consolidated into a nonwoven web. Consolidation can be achieved by methods that apply heat and/or pressure to the fibrous web, such as thermal spot (i.e., point) bonding. Thermal point bonding can be accomplished by passing the fibrous web through a pressure nip formed by two rolls, one of which is heated and contains a plurality of raised points on its surface, as is described in U.S. Pat. No. 3,855,046. Consolidation methods can also include, but are not limited to, ultrasonic bonding, through-air bonding, resin bonding, and hydroentanglement. Hydroentanglement typically involves treatment of the fibrous web with high pressure water jets to consolidate the web via mechanical fiber entanglement (friction) in the region desired to be consolidated, with the sites being formed in the area of fiber entanglement. The fibers can be hydroentangled as taught in U.S. Pat. Nos. 4,021,284 and 4,024,612.

All shapes of fibers may be used to form the nonwoven of the present invention. Nonwovens comprising "flat" fibers, such as fibers that are rectangular or oblong in cross section, however, may be better joined to the elastomeric film than nonwoven fabrics with fibers that are circular in cross section. Additionally, notched fibers may be used (i.e., multilobal, including bilobal and trilobal fibers).

The nonwoven of the present invention may have a basis weight of about 5 grams per square meter (gsm) to 75 gsm. In one embodiment, the nonwoven fabric has a basis weight from about 5 to about 30 gsm. Unless otherwise noted, basis weights disclosed herein are determined using European Disposables and Nonwovens Association ("EDANA") method 40.3-90.

Tie Layers of the Present Invention

Controlling the bond strength between the elastomeric film and the nonwoven of the inventive elastomeric laminate is an important aspect of the present invention. Bond strength may be measured using Mode II peel as described under Test Methods. Improved bond strength between the layers can be achieved by a number of ways, depending on the lamination method. If the layers are laminated by an adhesive method, the choice of adhesive, amount of adhesive, and pattern of adhesive applied to bond the layers can be adjusted to achieve the desired bond strength. Additionally, for EBLs of the present invention, bond strength between film and the nonwoven may be controlled by use of a tie layer (illustrated as A1 and A2 in FIG. 1) that may be selected to optimize (including increasing or decreasing the bond strength) the chemical affinity between the film and nonwoven. In particular, tie layers that contain copolymers of ethylene and propylene, or blends of ethylene- and propylene-based polymers, can be "tuned" to provide optimal chemical affinity with the nonwoven by appropriate choice of the copolymer's ethylene content. For example, in a laminate comprising a bicomponent nonwoven with a polyethylene sheath, a tie layer containing PE homopolymer may have too great a chemical affinity with the nonwoven whereas a tie layer containing PP homopolymer generally has too little chemical affinity. A tie layer comprising an ethylene-propylene copolymer with intermediate ethylene contents (10-97 wt. %) provides the chemical affinity required for optimal adhesion between film and nonwoven: enough adhesion to avoid delamination but not enough to cause unwanted pinholes in the film during the activation process.

When the layers making up the film are laminated by an extrusion lamination process, the properties of the film must be carefully selected to manage competing requirements of throughput, bonding, web tension and control, winding, unwinding, and activation, among others. In the case the extruded elastomeric film of the present invention is of thin gauge (less than about 30 gsm), the extruded film has less mass to retain heat during the extrusion process. Less mass means that the extruded molten laminate tends to solidify very rapidly. As discussed previously, this rapid solidification creates problems when trying to manufacture thinner films. Additionally, if the extruded elastomeric film solidifies too rapidly, it is harder to achieve adequate bond strength between the extruded elastomeric film and any nonwovens in an extrusion laminate. This is particularly a problem when the extruded polymer of the elastomeric film does not have great chemical affinity for the materials that comprise the nonwoven substrate. For instance, SBC elastomers do not have strong natural chemical affinity for the polyolefinic materials typically used for nonwoven substrates. In order to achieve adequate bond, laminates of SBC elastomers and nonwoven substrates must rely on mechanical bonding forces, such as those achieved by embedding the fibers of the nonwoven into the surface of the elastomeric film. Unfortunately, if the film has solidified before contacting the nonwoven, the fibers of the nonwoven cannot be embedded into the solidified surface of the film without application of significant pressure. Hence, the bond strength between the layers of the laminate is poor, and the elastomeric material will tend to delaminate easily. Furthermore, with the thin gauges of the elastomeric films of the present invention, any significant penetration of the fibers into the film, or deformation of the film from nip or other bonding pressure, may result in unacceptably thin regions of the film that may tear during subsequent processing or handling. In still other cases, the chemical affinity of the elastomeric film may be sufficiently high that an acceptable laminate bond strength is obtained, but the laminate may be difficult to activate due to a number of reasons that may include the intimate coupling of the nonwoven substrate and the film during the activation process. Furthermore, the high chemical affinity of the elastomeric film for the nonwoven may cause issues in storing, transporting and unwinding of the laminate, if the chemical affinity leads to roll blocking.

Regarding this problem, POE elastomers, however, have more chemical affinity for the polyolefinic materials in nonwoven, because the POEs are themselves polyolefinic materials. The chemical affinity of POEs for nonwovens means that these laminate layers are more apt to bond, even with little mechanical bonding from embedded nonwoven substrate fibers. In addition, because the thin POE-based films do not solidify as rapidly as the SBC-based materials, the extruded elastomeric film is still semi-molten and soft when it contacts the nonwoven, which allows the nonwoven fibers to embed into the film's surface. Hence, the inventors have observed that POE-based elastomeric films, or alternatively multilayer elastomeric films comprising POE-based tie layers, form laminates with stronger bond strength and less tendency to delaminate with bicomponent nonwovens comprising a PE sheath. The POE-based skin and tie layers of the present invention may be chosen in such a way as to optimize bonding to the nonwoven during the extrusion step of manufacture while providing a tack-free surface to allow winding and storage of bilaminate EBL with little roll blocking.

A further means to improve the bonding of a tie layer to a nonwoven in an EBL of the present invention is by control of the rate of crystallization of a polymer or blend of polymers comprising the tie layer. This has many advantages in the thin films of the present invention. When taken together with the chemical affinity of the tie layer for a surface of the nonwoven, the rate of crystallization may facilitate or limit the penetration of fibers into the surface. For example, when a blend of polymers is chosen with a high crystallization rate, an outer facing surface of the film may be reinforced and strengthened to resist deformation when contacting a fibrous surface of a nonwoven in the nip of an extrusion lamination process, with beneficial effects on the film quality. Of course, too rapid of a crystallization may result in an outer surface that is so resistant to flow that adequate contact with a nonwoven surface is not achieved. In another example, therefore, a polymer blend is chosen to reduce the rate of crystallization so that an outer facing surface of the film may remain soft and able to flow, increasing the contact area and contact time of a tie layer and nonwoven in an extrusion lamination process. One of ordinary skill in the art will recognize that the rate of crystallization may be further adjusted by means of nucleation aids, shear conditions, process temperature, plasticizers, and the like, and that the rate of crystallization may have limited or even no impact on the fusion index of EBLs useful in absorbent articles of the present invention. Crystallization rates of tie layers useful in EBLs of the present invention range from about 1 second to about 60 seconds, from about 3 seconds to about 30 seconds, or from about 5 seconds to about 20 seconds.

Skin Layers of the Present Invention

A challenge of using elastomeric films is that the polymers used to make the films are inherently sticky or tacky. When elastomeric films are extruded and wound into a roll, the film will tend to stick to itself or "block," thereby becoming difficult or impossible to unwind. Blocking becomes more pronounced as the film is aged or stored in a warm environment, such as inside a storage warehouse. A similar problem exists when an elastomeric film is extruded onto a nonwoven to make a bilaminate and wound onto a roll, since a tacky surface of the film will come into intimate contact with a substantial portion of an opposite surface of the bilaminate when wound. This may prevent unwinding of the roll at commercial speeds in the process of making absorbent articles and may lead to damage to the film, the nonwoven, or to both.

These problems can be addressed in a number of ways. For instance, antiblocking agents may be used. Antiblocking agents, which are usually inorganic particulate materials such as silica or talc, can be incorporated within one or more layers of the film. Antiblocking agents can also be dusted onto the outer surfaces of extruded film as the film is being formed. The elastomeric film can also be surface-coated with materials that are not sticky, such as a nonblocking polymer, a brittle nonblocking polymer, a surface coating such as a lacquer or ink, and other such powder coatings. Another way to solve this problem is to coextrude a non-tacky skin layer (illustrated as A2 in FIG. 1—when NW2 is not present) as part of the film. The skin layer may be identical (chemically and/or physically) to the tie layer. Thus, referring to FIG. 1, if NW2 is present, A2 may act as a second tie layer. If, however, A2 forms an exterior surface of the laminate, it may act as a skin layer. In the latter case, a nonwoven may be joined to it in a separate process later in time via an adhesive or other bonding means (including, thermal bonds, radio frequency bonds, pressure bonds, ultrasonic bonds, welds, stitching, and the like).

The fusion index for the tie and/or the skin layers of the present invention may be from about 14% to about 40%. The fusion index for the polyethylene portion of the nonwoven of the present invention may be from about 80% to about 100%. And, the fusion index for the polypropylene portion of the nonwoven of the present invention may be greater than about 50%. Further, the fusion index for the core layer of the present invention comprising thermoplastic polyolefin elastomers may be from about 10% to about 30%.

Skin layers of the present invention may comprise less than 20%, less than 15%, or less than 10% of the volume of an inner core layer. It may be desirable to have a skin layer and tie layer which are compositionally identical.

Draw Down Polymers of the Present Invention

One or a combination of layers of the EBL may comprise one or a combination of draw down polymers. In embodiments where one or a combination of draw down polymers are present in two or more layers, the amount of draw down polymer (in weight percent) in each layer may be equal or different. Further, the composition of a draw down polymer or blend of draw down polymers present in a first layer may be compositionally identical to or distinct from a draw down polymer or blend of draw down polymers present in a second layer. The draw down polymer is a polymer that adds or enhances one or more film properties or processing properties, such as those that aid in processability during film preparation. For example, the draw down polymer can aid in the production of reduced-gauge (i.e., thin) films. In some embodiments, the draw down polymer can aid in film extrusion, such as by helping to provide an increased line speed or reduce draw resonance. Other possible processability benefits from the addition of the draw down polymer include improving the melt curtain stability, providing a smooth film surface, providing a lower viscosity of the polymer melt, providing better resistance to heat (e.g., increasing the film's heat capacity or thermal stability), providing resistance to tearing, providing resistance to pinhole formation, providing a controlled and uniform thickness, or providing a homogeneous composition. The draw down polymer can act as a processing aid that lubricates the die to reduce sticking (e.g., of elastomeric polymers) and flow resistance of the molten elastomeric resin. Of course, the addition of the draw down polymer can provide one or a combination of these aids to film extrusion or processability.

There are many examples of draw down polymers. For example, a linear low-density polyethylene (e.g., ELITE™ 5800 provided by Dow Chemical Corp. of Midland, Mich.) can be added to a layer of the film composition to lower the viscosity of the polymer melt and enhance the processability of the extruded film. High-impact polystyrene (HIPS) (e.g., STYRON™ 485 from Dow Chemical Corp. of Midland, Mich.; IneosNova 473D from IneosNova of Channahon, Ill.) can help control the film modulus, improve the toughness of the film, and reduce the overall cost of the elastomeric material. Polypropylene can improve the robustness of the elastomer and improve the films' resistance to pinholing and tearing. Homopolymer polypropylene (hPP) (e.g., INSPIRE™ D118 from Dow Chemical Corp. of Midland, Mich.; Polypropylene 3622 from Total Petrochemicals of Houston, Tex.) can be added to improve processability. hPP is a form of polypropylene which is highly crystalline and containing essentially 100% propylene monomer. In some embodiments, hPP is added to a layer comprising an elastomeric polymer (e.g., styrene block copolymers), as discussed below; the addition can result, in some instances, in a film that can be extruded at a thinner gauge, with improved gauge uniformity, or with reduced tendency to experience draw resonance during extrusion.

The draw down polymers can be linear low density polyethylene, propylene, homopolymer polypropylene, high impact polystyrene, and mixtures thereof. The draw down polymer can be a polymer which has been prepared using a single-site catalyst such as a metallocene catalyst and can be, for example, a polyolefin produced using a metallocene catalyst (e.g., ELITE™ 5800 provided by Dow Chemical Corp. of Midland, Mich.). The identity and amount of draw down polymer can depend on the other components in the layer (e.g., the identity of the olefin-based elastomeric polymer(s) in the layer), other components of the film or, if applicable, components of the laminate that comprises the film. The total amount of draw down polymer can be present in an amount effective to enhance one or more film properties that aid in processability during film preparation; for example, the total amount of draw down polymer can be present in an amount effective to provide a film gauge of about 25 gsm, about 20 gsm, about 15 gsm, or about 10 gsm. The total amount of draw down polymer (i.e., the combined amount of the one or more draw down polymer(s)) can be at least about 5%, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, or about 95 wt % of a layer (i.e., total weight of draw down polymer(s) divided by the total weight of the layer). In some instances the total amount of the draw down polymer is at least about 5 wt %, at least about 10 wt %, at least about 20 wt %, or at least about 45 wt % of the EBL. A fuller description of draw down polymers and thin elastomeric films that are useful for making EBLs and absorbent articles of the present invention can be found in the U.S. Patent Application titled "Elastomeric Materials," filed Jan. 23, 2009, listing Iyad Muslet as the first named inventor, and using attorney docket number CLPP-07005.

Adhesives of the Present Invention

Referring to FIG. 1, an adhesive may be used between the NW1 and A1 and/or between A2 and NW2. The adhesive may be a hot-melt adhesive applied via a slot coater and/or sprayer, for example. According to one embodiment, the adhesive may be H2031, H2401, or H2861, which are commercially available from Bostik Inc. of Wauwatosa, Wis. Using adhesive assist, the adhesive may be applied during the fabrication of the EBL by applying it to a surface of the nonwoven (e.g., NW1) just prior to joining the film extrudate, particularly, the tie layer (e.g., A1). Further, a second nonwoven (e.g., NW2) may be adhesively laminated with an outer layer (e.g., A2) of an EBL according to the present invention. Still Further, the EBL of the present invention (which may include a first and second nonwoven (e.g., NW1 and NW2, respectively) may be adhesively joined to one or more components of an absorbent article, including an absorbent core, a waistband, a cuff, a topsheet, etc.

EBLS of the Present Invention

There are several physical properties of the extrusion bonded laminate of the present invention that impact making and storing it, as well as how the laminate performs as part of an absorbent article. For example, tackiness of the skin layer (A2) affects the ability to unwind the laminate after storage. Pinholes in the elastomeric layer resulting from the activation process may cause the laminate to become water permeable and may cause tearing of the laminate. If the bond strength of the layers is too strong, activation of the laminate may be compromised; if the bond strength is too weak, the layers of the laminate may delaminate. Further, tensile strength and hysteresis of the laminate may impact the integrity and fit of the absorbent article. Tables 5-8 illustrate several parameters of examples 1-26 (examples 5, 6, 12, 13, 19, 21 are comparative). Beyond the parameters illustrated in Tables 5-8, laminates useful in absorbent article of the present invention may have parameters as disclosed in the following paragraphs.

Laminates useful in absorbent article of the present invention may have a blocking force of less than about 0.4 N/cm, about 0.24 N/cm, or about 0.12 N/cm.

Laminates useful in absorbent article of the present invention may have a basis weight of from about 10 gsm to about 135 gsm, from about 20 gsm to about 100 gsm, from about 40 gsm to about 80 gsm, or from about 50 gsm to about 60 gsm.

Laminates useful in absorbent article of the present invention may be elastic to at least about 50%, about 70%, about 100%, and about 130% engineering strain.

Laminates useful in absorbent article of the present invention may have a laminate bond strength from about 0.5 to about 3.5 N/cm or from about 1 to about 2 N/cm (see Tensile Test (Mode II)).

Laminates useful in absorbent article of the present invention may have an ultimate tensile strength of greater than about 3 N/cm (see Tensile Test (Mode II)).

Laminates useful in absorbent article of the present invention may be free from pinholes. Laminates useful in absorbent article of the present invention may have a percent engineering strain at break from about 100% to about 500%, from about 120% to about 400%, or from about 150% to about 300%.

Laminates useful in absorbent article of the present invention, as well as the components that comprise them (e.g., an outer cover, a back or front ear, a side panel) may be elastic to at least about 50%, about 70%, about 100%, or about 130% engineering strain.

Laminates useful in absorbent article of the present invention may have a percent set less than about 12%, force relaxation less than about 40%, and a Cycle 1 unload force at 50% strain of greater than about 0.10 N/cm as measured by the two cycle hysteresis test. In some embodiments, the percent set of the laminate may be about 20% or less, about 15% or less, or about 10% or less as measured by the two cycle hysteresis test having a 75% strain first loading cycle and a 75% strain second loading cycle. In other embodiments, the percent set of the laminate may be about 20% or less, about 15% or less, or about 10% or less as measured by the two cycle hysteresis test.

Elastic laminates may be mechanically activated by one or a combination of activating means, including, activating the web through intermeshing gears or plates, activating the web through incremental stretching, activating the web by ring rolling, activating the web by tenter frame stretching, and activating the web in the machine direction between nips or roll stacks operating at different speeds. Incremental stretching rollers may be used to activate elastic laminates in the MD, CD, at an angle, or any combination thereof. In some embodiments, the depth of engagement used for incremental stretching is about 0.05 inches, about 0.10 inches, about 0.15 inches, about 0.20 inches, or about 0.25 inches. The depth of engagement can be, for example, at least about 0.05 inches or at least about 0.10 inches. The depth of engagement can be, for example, no more than about 0.10 inches, no more than about 0.18 inches, or no more than about 0.25 inches. The pitch of engagement can be, for example, from about 0.060 inches to about 0.200 inches, from about 0.080 inches to about 0.150 inches, or from about 0.100 inches to about 0.125 inches. Further, laminates may be activated at commercial rates via, for example, the ring rolling activation process. The activation may occur immediately after the extrusion lamination process or may occur as the laminate is unwound from a roll on which it was stored.

Absorbent Articles of the Present Invention

The laminate of the present invention may make up at least a portion of one or more components of an absorbent article, including a backsheet, an outer cover, a sidepanel, a waistband, a front- or back-ear, and combinations thereof. For instance, the laminate of the present invention may make up a portion of the pant or diaper outer cover disclosed in U.S. Pub. Nos. 2005/0171499, 2008/0208155, 2007/0167929, and 2008-0045917. The laminate may be subjected to additional processing steps before or after incorporation into an absorbent article. For example, one or more components of the absorbent article comprising the EBL may be activated by passing it through intermeshing wheels (ring rolls) to incrementally stretch and deform or break-up the nonwoven, tie, and/or skin layers. Further, one or more components of the absorbent article comprising the EBL may be apertured to improve air flow through the material and improve the comfort of the absorbent article when worn. The EBL may be printed, embossed, textured, or similarly modified to improve the aesthetics of the absorbent article or even to provide some function or feedback to the wearer.

Figure 2:
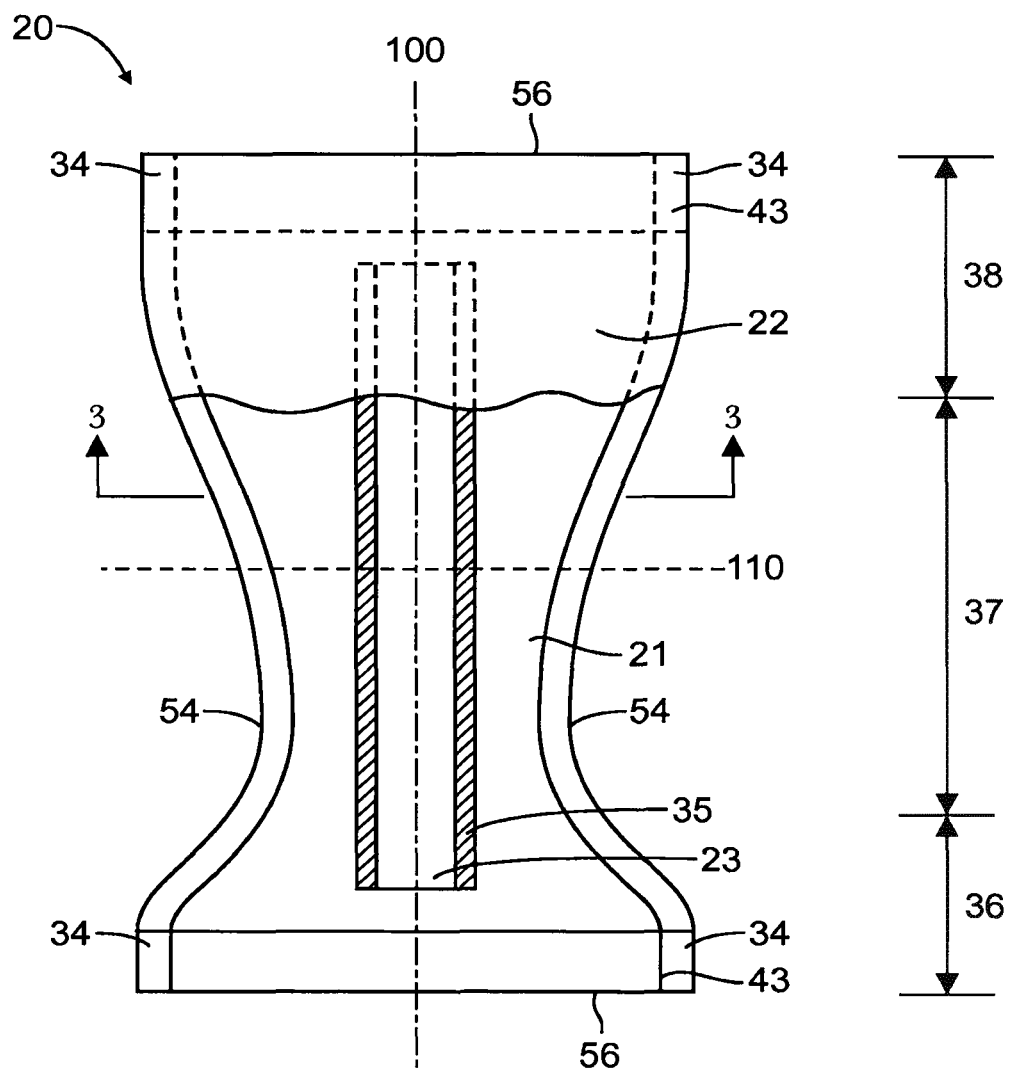
FIG. 2 is a top plan view of an absorbent article including an EBL of the present invention.
Figure 3:
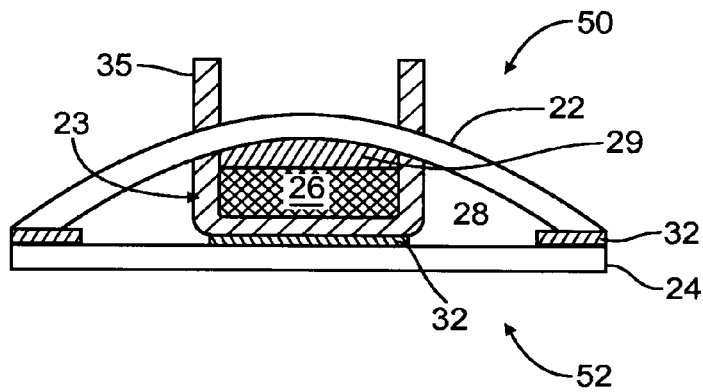
FIG. 3 is a sectional side view of the absorbent article of FIG. 2.

FIGS. 2 and 3 show an absorbent article (illustrated as a pant-like diaper 20) constructed in accordance with the present invention. The diaper 20 has a longitudinal centerline 100 and a lateral centerline 110. The diaper 20 defines an inner surface 50 and an opposing outer surface 52. The inner surface 50 generally includes that portion of the diaper 20 which is positioned adjacent the wearer's body during use (i.e., the wearer-facing side), while the outer surface 52 generally comprises that portion of the diaper 20 which is positioned away from the wearer's body (i.e., the garment-facing side).

The diaper 20, includes a chassis 21 having a first, or front, waist region 36, a second, or back, waist region 38 opposed to the front waist region 36, and a crotch region 37 located between the front waist region 36 and the back waist region 38. The waist regions 36 and 38 generally include those portions of the diaper 20 which, when the diaper 20 worn, encircle the waist of the wearer. The waist regions 36 and 38 can include elastic elements such that they gather about the waist of the wearer to provide improved fit and containment. The crotch region 37 is that portion of the diaper 20 which, when the diaper 20 is worn, is generally positioned between the legs of the wearer.

The outer periphery of the chassis 21 is defined by lateral end edges 56 that can be oriented generally parallel to the lateral centerline 110, and by longitudinal side edges 54 that can be oriented generally parallel to the longitudinal centerline 100 or, for better fit, can be curved or angled, as illustrated, to produce an "hourglass" shaped garment when viewed in a plan view. In some embodiments, the longitudinal centerline 100 can bisect the end edges 56 while the lateral centerline 110 can bisect the side edges 54.

The chassis 21 of the diaper 20 generally includes a liquid-permeable topsheet 22, an outer cover 24, and an absorbent core assembly 23 disposed between the topsheet 22 and the outer cover 24.

The core assembly 23 can be positioned on a wearer-facing surface of the outer cover 24. The core assembly 23 can be joined to the outer cover 24 via any suitable adhesive or cohesive 32 (as illustrated) or via any other suitable means known in the art (e.g., thermal bonds, radio frequency bonds, pressure bonds, ultrasonic bonds, welds, stitching, and the like). In some embodiments, the core assembly 23 is attached to the outer cover 24 in as few locations as possible; this can make the outer cover 24 look and feel softer. Suitable examples for attaching the core assembly 23 to the outer cover 24 include the attachment means described in U.S. Pub. No. 2007/0287982. Other Suitable examples for attaching the core assembly to the outer cover include the attachment means described U.S. Pub. No. 2007/0287983.

On the other hand, in order to make the design more tamper-resistant, it may be desirable to attach the core assembly 23 to the outer cover 24 along at least part, if not all, of the core assembly's 23 periphery; or a small distance (about 5-20 mm) inboard of the periphery. For example, the bond area between the core assembly 23 and the outer cover 24 can be less than about 70%, or, as another example, less than about 50%, or, as yet another example, less than about 20% of the core assembly 23 surface area that is attached to the outer cover 24.

The core assembly 23 is the portion of the diaper 20 providing much of the absorptive and containment function. The absorbent core assembly 23 includes an absorbent core 26, both of which can be disposed symmetrically or asymmetrically with respect to either or both of the longitudinal centerline 100 and/or the lateral centerline 110. As illustrated, the absorbent core 26 and core assembly 23 are symmetrical with respect to both the longitudinal centerline 100 and the lateral centerline 110.

The absorbent core 26 can include a wide variety of liquid-absorbent materials commonly used in disposable diapers and other absorbent articles. Examples of suitable absorbent materials include comminuted wood pulp (e.g., air felt creped cellulose wadding); melt blown polymers including co-form; chemically stiffened, modified or cross-linked cellulosic fibers; wraps and tissue laminates; absorbent foams; absorbent sponges; superabsorbent polymers; absorbent gelling materials; or any other known absorbent material or combinations of materials. The absorbent core 26 can include (1) a fluid-acquisition component which acquires fluid exudates and partitions the exudates away from a wearer's body, (2) a fluid-distribution component which redistributes fluid exudates to locations displaced from the point of initial exudate loading, and/or (3) a fluid-storage component which retains a majority of the fluid exudates on a weight basis. A suitable absorbent core comprising an acquisition layer, a distribution layer, and/or a storage layer is described in U.S. Pat. No. 6,013,589. A suitable absorbent core having minimal absorbent fibrous material (i.e., not more than about 20 wt. % based on the weight of the absorbent core) within the absorbent core is described in U.S. 2004/0167486. Other suitable absorbent core configurations are discussed in U.S. Pub. Nos. 2003/0225382, 2006/0155253, and 2006/0155254. It may be desirable to have an absorbent core and/or absorbent assembly that is free of or substantially free of any absorbent fibrous material (i.e., air-felt free) as described in U.S. Pub. No. 2005/0171499.

In some embodiments, the core assembly 23 can include a containment member 28, such that the absorbent core 26 is disposed between the topsheet 22 and the containment member 28. In some embodiments, the containment member 28 covers a garment-facing surface of the absorbent core 26, at least in part, and extends laterally beyond the core 26. The containment member 28 can also extend upwardly to cover the lateral sides of the absorbent core 26. The containment member 28 can be constructed from a woven web, a nonwoven web (with synthetic and/or natural fibers), an apertured film, and a composite or laminate of any of the aforementioned materials. In certain embodiments, the containment member 28 is an air permeable nonwoven web such as described in U.S. Pat. No. 4,888,231.

The absorbent core assembly can also include a core cover 29 disposed on a wearer-facing surface of the absorbent core 26. The core cover 29 can help immobilize the liquid absorbent material of the absorbent core 26. The core cover 29 may generally be a liquid pervious material, such as a nonwoven material or tissue.

The components of the core assembly 23 can be joined as described via any suitable adhesive or cohesive or via any other suitable means known in the art. Any of the aforementioned layers of the core assembly 23 can be a single material or can be a laminate or other combination of two or more materials.

As illustrated, the topsheet 22 is a distinct structural unit that covers the absorbent core 23 and may be attached to the outer cover 24, for example via the adhesive or cohesive 32, thereby forming an enclosure for the absorbent core. In an alternate embodiment (not shown), the core assembly 23 can be self-contained by integrating the topsheet 22 into the core assembly 23, for example by disposing the topsheet 22 adjacent a body-facing surface of the core cover 29. The topsheet 22 can be made from any suitable liquid-permeable material, for example those described in U.S. Pat. No. 3,860,003, U.S. Pat. No. 5,151,092, and U.S. Pat. No. 5,221,274.

As shown, a pair of opposing and longitudinally extending leg cuffs 35 are disposed on and extend outwardly from the topsheet 22. The leg cuffs 35 provide a seal against the wearer's body and improve containment of liquids and other body exudates. In the alternate embodiment (not shown) described above in which the core assembly 23 is self-contained and includes the topsheet 22, the leg cuffs 35 can simply be the extension of the laterally distal ends of the containment member 28.

The diaper 20 can also include a waistband 43 that generally forms at least a portion of the end edge 56 and/or a leg elastic (not shown) that generally forms at least a portion of the side edges 54. The waistband 43 and leg elastic are those portions of the diaper 20 which are intended to elastically expand and contract to dynamically fit the wearer's waist and legs, respectively, to provide improved fit and containment. The elastic waistband 43 can include a segment positioned in the front waist region 36 and/or the back waist region 38, and can be discretely attached or an integral part of the chassis 21 Examples of suitable waistbands include those described in U.S. Pat. No. 4,515,595, U.S. Pat. No. 5,151,092, and U.S. Pat. No. 5,221,274.

The diaper 20 can be preformed by the manufacturer to create a pull-on diaper or pant, and the diaper can be prefastened by the manufacturer or fastened by the consumer prior to wearing. Specifically, the diaper 20 may include left and right closed side seams 34, each disposed at regions proximal to the front and back ends of side edges 54. Each side seam 34 can be closed by buttressing and subsequently attaching a given side edge 54 in the front and back waist regions 36 and 38 either using a permanent seam or refastenable closure member. Suitable permanent seams include, for example, heat seals, adhesive bonds, ultrasonic bonds, high pressure bonds, radio frequency bonds, hot air bonds, heated point bonds, and combinations thereof. Suitable refastenable closure members include, for example, hook and loop fasteners, hook and hook fasteners, macrofasteners, tape fasteners, adhesive fasteners, cohesive fasteners, magnetic fasteners, hermaphrodidic fasteners, buttons, snaps, and tab and slot fasteners. The side edges 54 can alternatively be attached in an exterior surface-to-exterior surface configuration, interior surface-to-interior surface configuration, or interior surface-to-exterior surface (overlapping) configuration.

When in use, the pull-on diaper 20 is worn on the lower torso of a wearer, such that the end edges 56 encircle the waist of the wearer while, at the same time, the chassis side edges 54 define leg openings that receive the legs of the wearer. The crotch region 37 is generally positioned between the legs of the wearer, such that the absorbent core 26 extends from the front waist region 36 through the crotch region 37 to the back waist region 38.

In another embodiment (not shown), the principles of the present invention as described above with respect to pant-like garments can be equally applied to absorbent articles that are configured as taped diapers. In this embodiment, the diapers are not closed prior to wearing. Instead, the diapers generally include side panels having engaging elements. The side panels can be attached to the diaper chassis at either or both of the front and rear waist regions such that the engaging elements, when worn, contact some portion of the diaper on the opposing waist region to seal the diaper. Examples of suitable diapers according to the present invention are described in U.S. Pub. No. 2008/0114326.

EXAMPLES OF THE PRESENT INVENTION

Examples of extrusion bonded laminates are described in Tables 1, 2, 3 and 9 (bi-laminate with one nonwoven) and Tables 4 and 10 (tri-laminate with two nonwovens) which provide the details of the film structure (monolayer or multilayer), film composition, film basis weight and nonwoven of each example. The examples of Tables 4 and 10 can be read in conjunction with FIG. 1, which illustrates a first nonwoven (NW1), a film comprising a tie layer (A1), a core layer (B), and a skin layer or a second tie layer (A2), as well as a second nonwoven (NW2). The composition of the film core of all examples (except examples 5 and 12) is a weight % blend of 92% VISTAMAXX 6102 (available from ExxonMobil, Houston Tex.), 1% Ampacet 10562 (process aid) and 7% Ampacet 110361 (white masterbatch with 70% TiO$_2$). Ampacet materials are available from Ampacet Corporation, Cincinnati, Ohio. The composition of the film core of examples 5 and 12 is a weight % blend of 92% Infuse 9107 (available from The Dow Chemical Company of Midland, Mich.), 1% Ampacet 10562 and 7% Ampacet 110361. Examples 5, 12, 6, 13, 19 and 21 are extrusion bonded laminates with a monolayer film with no tie layer (A$_1$) and no skin layer (A$_2$). Example 7 and 14 are extrusion bonded laminates with a core film and a skin layer (BA$_2$), and do not have a tie layer (no A$_1$); the skin layer (A$_2$) is a weight % blend of 82% Elite 5800 (draw down polymer) (available from The Dow Chemical Company of Midland, Mich.), 9% Fina 3868 (available from Total Petrochemicals of Houston, Tex.), 1% Luvofilm 9679 (available from Lehmann & Voss & Company, Hamburg, Germany) and 8% PE 20 S (antiblock available from Polytechs SAS, Cany Barville, France). Example 25 and 26 are extrusion bonded laminates with a core film and a skin layer (BA$_2$), and do not have a tie layer (no A$_1$); the skin layer (A$_2$) is a weight % blend of 50% Elite 5800 (draw down polymer), 32% Equistar M6060 (available from Equistar Chemicals, LP, Cincinnati, Ohio, a subsidiary of Lyondell-Basell Industries), 9% Fina 3868, 1% Luvofilm 9679 and 8% Polytech PE 20 S.

Examples 1, 2, 3, 4, 8, 9, 10, 11, 20, 22, 27, 28, 29, 30, 31, 32 and 33 of Tables 1, 2, 3, and 9 can be read in conjunction with FIG. 7, which illustrates a first nonwoven (NW1), a film comprising a tie layer (A1), a core layer (B), and a skin layer (A2), wherein A1 and A2 are extruded from a first extruder and the B is simultaneously co-extruded from a second extruder such that the A1, A2, and B layers are joined together. And, the NW1 is simultaneously unwound and joined to the A1 layer. In these examples, A2 performs as a skin layer. These are examples of EBLs with a multilayer film (A1BA2) comprising a tie layer (A1) and a skin layer (A2), where the composition of A1 is compositionally identical to A2. The tie layers used in examples 1, 2, 3, 4, 8, 9, 10, 11 15, 16, 17, 18, and 27 to 40 are a weight % blend of Infuse 9107, Ampacet 10562 and Elite 5800 (draw down polymer) and are selected to improve the bonding of the film to the bicomponent (PP/PE, core/sheath) nonwoven in order to reduce the occurrence of delamination. The actual weight % amounts for each skin layer formula are shown in Tables 1, 2, 3, 4, 9 and 10. The tie layer used in examples 20, 22, 23 and 24 is a weight % blend of 59% VISTAMAXX 6102, 1% Ampacet 10562 and 40% Adflex V109F (available from Basell USA Inc., Elkton, Md. or Laporte, Tex.) and is selected to decrease the bond strength of the film to the monofilament, PP based Sofspan 200 nonwoven in order to improve the activation survivability of the extrusion laminate (for example, to minimize or eliminate the formation of unwanted pin holes during activation).

The process conditions used to produce the different extrusion laminate examples are not identical. The process conditions adjusted to provide uniform film include melt temperature, line speed and gap between the two combining rolls (controlled by pressure or gap distance) and are shown in Tables 1, 2, 3, 4, 9 and 10. Examples 1 to 14, 19 to 22, and 25 to 33 are extrusion bonded laminates with one nonwoven that are subjected to activation on a high speed research press (HSRP) as described in U.S. Pat. Nos. 7,062,983 and 6,843,134. Activation in the described simulated ring rolling process refers to using aluminum plates with inter-meshing teeth to selectively stretch portions of the laminate such that the nonwoven is broken and/or elongated and the elastic film is able to extend and retract without being unduly encumbered by the nonwoven. The laminates useful in the absorbent articles of the present invention may be activated with the elongation imparted in the cross direction (CD) with a target engineering strain of about 206% (for example with a pair of flat plates with intermeshing teeth having a depth of engagement of about 3.56 mm and a pitch of about 2.49 mm) or a target engineering strain of about 226% (for example with a pair of flat plates with intermeshing teeth having a depth of engagement of about 3.81 mm and a pitch of about 2.49 mm) or a target engineering strain of about 245% (for example with a pair of flat plates with intermeshing teeth having a depth of engagement of about 4.06 mm and a pitch of about 2.49 mm) or a target engineering strain of about 265% (for example with a pair of flat plates with intermeshing teeth having a depth of engagement of about 4.32 mm and a pitch of about 2.49 mm). The EBL examples are mechanically activated using activation plates having inter-meshing teeth with a tip radius of 0.1 mm, a root radius of 0.5 mm and tooth height of 10.15 mm. Additional details of activation with the HSRP are shown in Tables 1, 2, 3, and 9 (activation pitch, target maximum activation strain rate, depth of engagement and average % engineering strain of activation). The activated EBLs are allowed to age a minimum of 1 day at 23±2° C. before testing the physical properties. Examples 1 to 14 are films extrusion bond laminated to a bicomponent PE/PP (70/30, core/sheath), 18 gsm nonwoven from Fiberweb (Washougal, Wash.). Examples 27 to 33 are films extrusion bond laminated to a bicomponent PE/PP (70/30, core/sheath), 15 gsm nonwoven from Fiberweb (Washougal, Wash.). Examples 25 and 26 are films extrusion bond laminated to a bicomponent PE/PP (core/sheath), 18 gsm nonwoven from Fiberweb (Peine, Germany). The function of the tie layer (examples 1 to 4, 8 to 11, and 27 to 33) is to improve the laminate bond strength between the bicomponent nonwoven and the film. Examples 19 to 22 are films extrusion bond laminated to a 22 gsm monofilament PP based nonwoven from Fiberweb (Biesheim, France) and the function of the tie layer (examples 20 and 22) is to reduce the laminate bond strength to enable better activation survivability. Examples 1 to 14, 19 to 22, and 25 to 33 are made without the addition of adhesive.

TABLE 1

| | Examples | | | | | | | |
|---|---|---|---|---|---|---|---|---|
| | 1 | 2 | 3 | 4 | 5 | 6 | 7 | 25 |
| NW1[1] | 1 | 1 | 1 | 1 | 1 | 1 | 1 | 4 |
| A1: weight % (Infuse 9107/Ampacet 10562/Elite 5800) | 99/1/0 | 84/1/15 | 69/1/30 | 0/1/99 | — | — | — | — |
| B[2] | VM blend | VM blend | VM blend | VM blend | Infuse blend | VM blend | VM blend | VM blend |
| A2: weight % (Infuse 9107/Ampacet 10562/Elite 5800) | 99/1/0 | 84/1/15 | 69/1/30 | 0/1/99 | — | — | — | — |
| A2: weight % (Elite 5800/Fina 3868/luvofilm 9679/Polytech PE 20S) | — | — | — | — | — | — | 82/9/1/8 | — |
| A2: weight % (Elite 5800/Equistar M6060/Fina 3868/luvofilm 9679/Polytech PE 20S) | — | — | — | — | — | — | — | 50/32/9/1/8 |
| NW2 | — | — | — | — | — | — | — | — |
| A1 = A2 | yes | yes | yes | yes | — | — | — | — |
| total film basis weight | 25 gsm | 25 gsm | 25 gsm | 25 gsm | 25 gsm | 25 gsm | 29 gsm | 22 gsm |
| film basis weight (gsm) A1/B/A2 | 3/19/3 | 3/19/3 | 3/19/3 | 3/19/3 | 0/25/0 | 0/25/0 | 0/25/4 | 0/18/4 |
| Adhesive used? | NO | NO | NO | NO | NO | NO | NO | NO |
| Melt temperature (° F.) | 460 | 457 | 455 | 460 | 515 | 450 | 450 | 416 |
| Line speed (feet per minute) | 235 | 235 | 235 | 238 | 230 | 200 | 247 | 260 |
| Nip pressure (psi) or Nip Gap (CC) at combining Rolls[3] | CC | CC | CC | CC | CC | 50 psi | 80 psi | CC |
| Details of High Speed Research Press (HSRP) activation | | | | | | | | |
| target maximum activation strain rate (sec$^{-1}$) | 570 | 570 | 570 | 570 | 570 | 229 | 229 | 229 |
| HSRP activation pitch (inches) | 0.098" | 0.098" | 0.098" | 0.098" | 0.098" | 0.098" | 0.098" | 0.098" |
| Depth of engagement (DOE) inches | 0.140" | 0.140" | 0.140" | 0.140" | 0.140" | 0.140" | 0.140" | 0.140" |
| Average Strain of activation (%) | 206% | 206% | 206% | 206% | 206% | 206% | 206% | 206% |

[1] NW1 = 1 = 18 gsm (70/30 core/sheath, PP/PE) bicomponent spunbond, produced at Fiberweb (Washougal, Washington). NW1 = 4 = 18 gsm PP/PE core/sheath bicomponent spunbond, #07-HH18-01 from Fiberweb (Peine, Germany)
[2] VM blend = Vistamaxx 6102 (92%), Ampacet 10562 (1%), Ampacet 110361 (7%) in weight %. Infuse blend = Infuse 9107 (92%), Ampacet 10562 (1%), Ampacet 110361 (7%) in weight %
[3] Nip gap in controlled compression (CC) is the gap between the two combining rolls and is approximately the thickness of the materials pressed in the opening (~0.005").

TABLE 2

| | Examples | | | | | | | |
|---|---|---|---|---|---|---|---|---|
| | 8 | 9 | 10 | 11 | 12 | 13 | 14 | 26 |
| NW1[1] | 1 | 1 | 1 | 1 | 1 | 1 | 1 | 4 |
| A1: weight % (Infuse 9107/Ampacet 10562/Elite 5800) | 99/1/0 | 84/1/15 | 69/1/30 | 0/1/99 | — | — | — | — |
| B[2] | VM blend | VM blend | VM blend | VM blend | Infuse blend | VM blend | VM blend | VM blend |
| A2: weight % (Infuse 9107/Ampacet 10562/Elite 5800) | 99/1/0 | 84/1/15 | 69/1/30 | 0/1/99 | — | — | — | — |
| A2: weight % (Elite 5800/Fina 3868/luvofilm 9679/Polytech PE 20S) | — | — | — | — | — | — | 82/9/1/8 | — |
| A2: weight % (Elite 5800/Equistar M6060/Fina 3868/luvofilm 9679/Polytech PE 20S) | — | — | — | — | — | — | — | 50/32/9/1/8 |
| NW2 | — | — | — | — | — | — | — | — |
| A1 = A2 | yes | yes | yes | yes | — | — | — | — |
| total film basis weight | 25 gsm | 25 gsm | 25 gsm | 25 gsm | 25 gsm | 25 gsm | 29 gsm | 22 gsm |
| film basis weight (gsm) A1/B/A2 | 3/19/3 | 3/19/3 | 3/19/3 | 3/19/3 | 0/25/0 | 0/25/0 | 0/25/4 | 0/18/4 |
| Adhesive used? | NO | NO | NO | NO | NO | NO | NO | NO |
| Melt temperature (° F.) | 460 | 457 | 455 | 460 | 515 | 450 | 450 | 416 |
| Line speed (feet per minute) | 235 | 235 | 235 | 238 | 230 | 200 | 247 | 260 |
| Nip pressure (psi) or Nip Gap (CC) at combining Rolls[3] | CC | CC | CC | CC | CC | 50 psi | 80 psi | CC |
| Details of High Speed Research Press (HSRP) activation | | | | | | | | |
| target maximum activation strain rate (sec$^{-1}$) | 638 | 638 | 638 | 638 | 638 | 256 | 256 | 256 |
| HSRP activation pitch (inches) | 0.098" | 0.098" | 0.098" | 0.098" | 0.098" | 0.098" | 0.098" | 0.098" |
| Depth of engagement (DOE) inches | 0.160" | 0.160" | 0.160" | 0.160" | 0.160" | 0.160" | 0.160" | 0.160" |
| Average Strain of activation (%) | 245% | 245% | 245% | 245% | 245% | 245% | 245% | 245% |

[1] NW1 = 1 = 18 gsm (70/30 core/sheath, PP/PE) bicomponent spunbond, produced at Fiberweb (Washougal, Washington). NW1 = 4 = 18 gsm PP/PE core/sheath bicomponent spunbond, #07-HH18-01 from Fiberweb (Peine, Germany)
[2] VM blend = Vistamaxx 6102 (92%), Ampacet 10562 (1%), Ampacet 110361 (7%) in weight %. Infuse blend = Infuse 9107 (92%), Ampacet 10562 (1%), Ampacet 110361 (7%) in weight %
[3] Nip gap in controlled compression (CC) is the gap between the two combining rolls and is approximately the thickness of the materials pressed in the opening (~0.005").

TABLE 3

| | Examples | | | |
|---|---|---|---|---|
| | 19 | 20 | 21 | 22 |
| NW1[1] | 3 | 3 | 3 | 3 |
| A1: weight % (Vistamaxx 6102/Ampacet 10562/Adflex V109F) | — | 59/1/40 | — | 59/1/40 |
| B[2] | VM blend | VM blend | VM blend | VM blend |
| A2: weight % (Vistamaxx 6102/Ampacet 10562/Adflex V109F) | — | 59/1/40 | — | 59/1/40 |
| NW2 | — | — | — | — |
| A1 = A2 | — | yes | — | yes |
| total film basis weight | 25 gsm | 25 gsm | 25 gsm | 25 gsm |
| film basis weight (A1/B/A2) | 0/25/0 | 3/19/3 | 0/25/0 | 3/19/3 |
| Adhesive used? | NO | NO | NO | NO |
| Melt temperature (° F.) | 462 | 462 | 462 | 462 |
| Line speed (feet per minute) | 230 | 230 | 230 | 230 |
| Nip pressure (psi) or Nip Gap (CC) at combining Rolls[3] | CC | CC | CC | CC |
| Details of High Speed Research Press (HSRP) activation | | | | |
| target maximum activation strain rate (sec$^{-1}$) | 570 | 570 | 638 | 638 |
| HSRP activation pitch (inches) | 0.098" | 0.098" | 0.098" | 0.098" |
| Depth of engagement (DOE) inches | 0.140" | 0.140" | 0.160" | 0.160" |
| Average Strain of activation (%) | 206 | 206 | 245 | 245 |

[1]NW1 = 3 = 22 gsm monofilament spunbond, Sofspan 200, produced at Fiberweb (Biesheim, France).
[2]VM blend = Vistamaxx 6102 (92%), Ampacet 10562 (1%), Ampacet 110361 (7%) in weight %.
[3]Nip gap in controlled compression (CC) is the gap between the two combining rolls and is approximately the thickness of the materials pressed in the opening (~0.005").

Examples of extrusion bonded laminates with two nonwovens are shown in Tables 4 and 10, which describes the film structure (monolayer or multilayer), film composition, film basis weight and nonwoven of each example, which can be read in conjunction with FIG. 6A. In examples 15, 16, 17, 18, 23, 24, and 34 to 40 the aged roll of extrusion bilaminate is combined with a second nonwoven (e.g., NW2) using an adhesive lamination process, with the addition of approximately 4.5 gsm of a Bostik adhesive to the A2 film-NW2 interface, followed by mechanically activation by a ring rolling activation process at a line speed of about 5.3 meter per second, to form a trilaminate (activation details are shown in Tables 4 and 10). Bostik H2031 adhesive was used to prepare examples 15, 16, 17, 18, 23 and 24. Bostik H2861 adhesive was used to prepare examples 34 to 40. The EBLs of said examples are allowed to age a minimum of 1 day at 23±2° C. after fabrication before the adhesive lamination process to produce the trilaminate. The activated trilaminate samples are allowed to age a minimum of 1 day at 23±2° C. before testing the physical properties (for example, the tensile test and the two cycle hysteresis test).

TABLE 4

| | Examples | | | | | |
|---|---|---|---|---|---|---|
| | 15 | 16 | 17 | 18 | 23 | 24 |
| NW1[1] | 1 | 1 | 1 | 1 | 3 | 3 |
| A1: weight % (Infuse 9107/Ampacet 10562/Elite 5800) | 69/1/30 | 69/1/30 | 0/1/99 | 0/1/99 | — | — |
| A1: weight % (Vistamaxx 6102/Ampacet 10562/Adflex V109F) | — | — | — | — | 59/1/40 | 59/1/40 |
| B[2] | VM blend | VM blend | VM blend | VM blend | VM blend | VM blend |
| A2: weight % (Infuse 9107/Ampacet 10562/Elite 5800) | 69/1/30 | 69/1/30 | 0/1/99 | 0/1/99 | — | — |
| A2: weight % (Vistamaxx 6102/Ampacet 10562/Adflex V109F) | — | — | — | — | 59/1/40 | 59/1/40 |
| NW2[4] | 2 | 2 | 2 | 2 | 2 | 2 |
| A1 = A2 | yes | yes | yes | yes | yes | yes |
| total film basis weight | 25 gsm | 25 gsm | 25 gsm | 25 gsm | 25 gsm | 25 gsm |
| film basis weight (gsm) A1/B/A2 | 3/19/3 | 3/19/3 | 3/19/3 | 3/19/3 | 3/19/3 | 3/19/3 |
| Melt temperature (° F.) | 455 | 455 | 460 | 460 | 462 | 462 |
| Line speed (feet per minute) | 235 | 235 | 238 | 238 | 230 | 230 |
| Nip pressure (psi) or Nip Gap (CC) at combining Rolls[3] | CC | CC | CC | CC | CC | CC |
| Details of On-line High Speed lamination and activation | | | | | | |
| Interface with Adhesive | A2-NW2 | A2-NW2 | A2-NW2 | A2-NW2 | A2-NW2 | A2-NW2 |
| Adhesive type (Bostik) | H2031 | H2031 | H2031 | H2031 | H2031 | H2031 |
| Adhesive basis weight (gsm) | 4.5 gsm | 4.5 gsm | 4.5 gsm | 4.5 gsm | 4.5 gsm | 4.5 gsm |
| Nip Gap | 0.005" | 0.005" | 0.005" | 0.005" | 0.005" | 0.005" |
| line speed (m/sec) | 5.33 | 5.33 | 5.33 | 5.33 | 5.33 | 5.33 |
| activation pitch (inches) | 0.100" | 0.100" | 0.100" | 0.100" | 0.100" | 0.100" |
| Depth of engagement (DOE) inches | 0.160" | 0.170" | 0.160" | 0.170" | 0.160" | 0.170" |
| Average Strain of activation (%) | 245 | 265 | 245 | 265 | 245 | 265 |

[1]NW1 = 1 = 18 gsm (70/30 core/sheath, PP/PE) bicomponent spunbond, produced at Fiberweb (Washougal, Washington). NW1 = 3 = 22 gsm monofilament spunbond, Sofspan 200, produced at Fiberweb (Biesheim, France).
[2]VM blend = Vistamaxx 6102 (92%), Ampacet 10562 (1%), Ampacet 110361 (7%) in weight %.
[3]Controlled compression (CC) nip gap is the gap between the two combining rolls and is about the thickness of the materials pressed in the opening (~0.005").
[4]NW2 = 2 = 20 gsm (70/30 core/sheath, PP/PE) bicomponent spunbond, produced at Fiberweb (Washougal, Washington).

The tensile properties of the extrusion laminate examples 1 to 7 and 25 (activated on the HSRP to 0.140" DOE at 0.098" pitch) are shown in Table 5. The tensile properties of the extrusion laminate examples 8 to 14 and 26 (activated on the HSRP to 0.160" DOE at 0.098" pitch) are shown in Table 6. The tensile properties of the extrusion laminate examples 27 to 33 (activated on the HSRP to 0.150" or 0.160" DOE at 0.098" pitch) are shown in Table 11. Examples 1 to 14, 25 and 26, made with a bicomponent PP/PE (core/sheath) nonwoven, have a basis weight of ~50 gsm or less, have an ultimate tensile strength>3 N/cm and most have stretch at 1 N/cm that is >70% engineering strain and for some examples >100% engineering strain or >120% engineering strain. Examples 27 to 33, made with a bicomponent PP/PE (core/sheath) nonwoven, have a basis weight of ~45 gsm or less, have an ultimate tensile strength>2.8 N/cm and most have stretch at 1 N/cm that is >100% engineering strain and for some examples >120% engineering strain. Examples 7 and 14, with a skin layer and without a tie layer, are examples where the stretch is lower (62% and 82% respectively) and coincides with a higher permanent set following activation. The Mode II failure forces of extrusion laminates with a tie layer (2.2-3.3 N/cm for examples 1 to 4, 8 to 11, and 27 to 33) are higher than the Mode II failure forces of extrusion laminate without the tie layer (1.0-1.6 N/cm for examples 5 to 7 and 12 to 14, 25 and 26), which demonstrates that the tie layer increases the bond strength between the film and the bicomponent nonwoven.

After activation, the extrusion laminates are inspected visually for pin holes by stretching the material to about 20% engineering strain (for example, a sample with 100 mm CD length is stretch to about 120 mm CD length). The nonwoven of examples 13 and 14 do not delaminate easily from the film, however pin holes with a diameter>about 1 mm are observed in the extrusion laminate. Examples 13 and 14 are produced with pressure at the nip (50 psi and 80 psi, respectively) and the nonwoven fibers penetrated into the film surface which may cause weak spots in the film and the formation of pin holes in the extrusion laminate during activation. Conversely, the nonwoven of examples 25 and 26 (produced in control compression mode) delaminates easily from the film and no pin holes with a diameter>about 1 mm are observed. The use of a tie layer in the extrusion laminates enables a good balance between stretch, laminate bond strength and activation survivability (no delamination or unwanted pin holes). Examples 1 to 4, 9 to 11 and 27 to 33 (with a tie layer) have good CD stretch after activation, are well bonded (as mentioned above), do not delaminate and are substantially free of holes having a diameter of greater in size than about 1 mm.

TABLE 5

| | Examples | | | | | | | |
|---|---|---|---|---|---|---|---|---|
| | 1 | 2 | 3 | 4 | 5 | 6 | 7 | 25 |
| basis weight (gsm) | 48 | 49 | 48 | 43 | 43 | 44 | 42 | 37 |
| Tensile Test Results | | | | | | | | |
| Stretch at 1 N/cm (% engineering strain) | 81 | 79 | 85 | 97 | 118 | 105 | 62 | 102 |
| Ultimate tensile strength (N/cm) | 3.8 | 4.0 | 3.3 | 3.2 | 5.1 | 4.3 | 4.2 | 3.5 |
| Mode II failure force (N/cm) | 3.2 | 3.3 | 3.0 | 2.3 | 1.2 | 1.1 | 1.6 | 1.0 |

TABLE 6

| | Examples | | | | | | | |
|---|---|---|---|---|---|---|---|---|
| | 8 | 9 | 10 | 11 | 12 | 13 | 14 | 26 |
| basis weight (gsm) | 50 | 50 | 47 | 44 | 43 | 45 | 42 | 38 |
| Tensile Test Results | | | | | | | | |
| Stretch at 1 N/cm (% engineering strain) | 109 | 102 | 106 | 122 | 144 | 138 | 82 | 129 |
| Ultimate tensile strength (N/cm) | 3.5 | 3.8 | 3.1 | 3.8 | 5.3 | 4 | 3.4 | 3.4 |
| Mode II failure force (N/cm) | 3.3 | 3.2 | 3.0 | 2.5 | 1.2 | 1.1 | 1.6 | 1.0 |

The tensile properties of the extrusion laminate examples 19 and 20 (activated on the HSRP to 0.140" DOE at 0.098" pitch) and 21 and 22 (activated on the HSRP to 0.160" DOE at 0.098" pitch) are shown in Table 7. Examples 19 to 22 (made with a monofilament Sofspan 200 nonwoven) have a basis weight of ~55 gsm or less, have an ultimate tensile strength ranging from 1.6 N/cm to 2.7 N/cm and have stretch at 1 N/cm that is >100% engineering strain and for some examples >135% engineering strain or >160% engineering strain. The Mode II failure forces of extrusion laminates with a tie layer (1.2-1.3 N/cm for examples 20 and 22) are lower than the Mode II failure forces of extrusion laminate without the tie layer (1.6-2.0 N/cm for examples 19 and 21), which demonstrates that the tie layer decreases the bond strength between the film and the monofilament nonwoven.

TABLE 7

| | Examples | | | |
|---|---|---|---|---|
| | 19 | 20 | 21 | 22 |
| basis weight (gsm) | 52 | 49 | 54 | 48 |
| Tensile Test Results | | | | |
| Stretch at 1 N/cm (% engineering strain) | 114 | 138 | 139 | 166 |
| Ultimate tensile strength (N/cm) | 2.4 | 1.8 | 2.7 | 1.6 |
| Mode II failure force (N/cm) | 1.6 | 1.2 | 2.0 | 1.3 |

The tensile properties of the extrusion laminate examples 15, 17 and 23 (activated on-line to 0.160" DOE at 0.100" pitch) and 16, 18 and 24 (activated on-line to 0.170" DOE at 0.100" pitch) are shown in Table 8. The tensile properties of the extrusion laminate examples 34, 36 and 38 (activated on-line to 0.150" DOE at 0.100" pitch) and examples 35, 37, 39 and 40 (activated on-line to 0.160" DOE at 0.100" pitch) are shown in Table 12. The trilaminate examples 15, 16, 17, 18, 23, 24, and 34 to 40 have an ultimate tensile strength of >3.2 N/cm and a strain at break of >250% engineering strain. The two cycle hysteresis results for examples 15, 16, 17, 18, 23 and 24 are also shown in Table 8. The two cycle hysteresis results for examples 34 to 40 are also shown in Table 12. The recoverable properties of the extrusion laminates, as measured by the 2 Cycle Hysteresis Test, are demonstrated by the unload forces at low engineering strain and the low percent set. For examples 15, 16, 17, 18, 23 and 24, the forces measured in the return cycle of the first cycle (C1 unload forces) are ≧0.15 N/cm at 50% engineering strain and ≧0.06 N/cm at 30% engineering strain. For examples 34 to 40, the forces measured in the return cycle of the first cycle (C1 unload forces) are ≧0.12 N/cm at 50% engineering strain and ≧0.05 N/cm at 30% engineering strain. The low percent set (≦10% for examples 15, 16, 17, 18, 23 and 24 and ≦12% for examples 34 to 40) after stretching to 130% engineering strain, shows that the extrusion laminates have desirable elastic properties. Additionally, the force relaxation of these extrusion laminates (examples 15, 16, 17, 18, 23, 24, and 34 to 40), measured at 130% engineering strain, is <40% force relaxation.

TABLE 8

| | Examples | | | | | |
|---|---|---|---|---|---|---|
| | 15 | 16 | 17 | 18 | 23 | 24 |
| basis weight (gsm) | 67 | 65 | 66 | 67 | 73 | 73 |
| 2 Cycle Hysteresis (130% engineering strain) Results (C1 = Cycle 1) | | | | | | |
| C1 Load force at 100% strain (N/cm) | 1.11 | 0.95 | 1.16 | 0.96 | 0.89 | 0.76 |
| C1 Unload force at 50% strain (N/cm) | 0.16 | 0.15 | 0.15 | 0.15 | 0.20 | 0.18 |
| C1 Unload force at 30% strain (N/cm) | 0.08 | 0.07 | 0.08 | 0.07 | 0.11 | 0.10 |
| % SET (% strain) | 9 | 10 | 9 | 9 | 8 | 8 |
| Force Relaxation (%) | 38.5 | 36.6 | 38.2 | 36.2 | 36.6 | 33.2 |
| Tensile Test Results | | | | | | |
| Ultimate tensile strength (N/cm) | 4.0 | 3.9 | 4.5 | 3.9 | 3.2 | 3.2 |
| Strain at break (% engineering strain) | 269 | 265 | 278 | 261 | 313 | 277 |

TABLE 9

| | Examples | | | | | | |
|---|---|---|---|---|---|---|---|
| | 27 | 28 | 29 | 30 | 31 | 32 | 33 |
| NW1[1] | 1 | 1 | 1 | 1 | 1 | 1 | 1 |
| A1: weight % (Infuse 9107/Ampacet 10562/Elite 5800) | 69/1/30 | 69/1/30 | 46/1/53 | 46/1/53 | 24/1/75 | 24/1/75 | 0/1/99 |
| B[2] | VM blend | VM blend | VM blend | VM blend | Infuse blend | VM blend | VM blend |
| A2: weight % (Infuse 9107/Ampacet 10562/Elite 5800) | 69/1/30 | 69/1/30 | 46/1/53 | 46/1/53 | 24/1/75 | 24/1/75 | 0/1/99 |
| NW2 | — | — | — | — | — | — | — |
| A1 = A2 | yes | yes | yes | yes | yes | yes | yes |
| total film basis weight | 25 gsm | 25 gsm | 25 gsm | 25 gsm | 25 gsm | 25 gsm | 25 gsm |
| film basis weight (gsm) A1/B/A2 | 3/19/3 | 3/19/3 | 3/19/3 | 3/19/3 | 3/19/3 | 3/19/3 | 3/19/3 |
| Adhesive used? | NO | NO | NO | NO | NO | NO | NO |
| Melt temperature (° F.) | 422 | 422 | 420 | 420 | 423 | 423 | 417 |
| Line speed (feet per minute) | 314 | 314 | 316 | 316 | 317 | 317 | 322 |
| Nip pressure (psi) or Nip Gap (CC) at combining Rolls[3] | CC | CC | CC | CC | CC | CC | CC |

TABLE 9-continued

|  | Examples | | | | | | |
|---|---|---|---|---|---|---|---|
|  | 27 | 28 | 29 | 30 | 31 | 32 | 33 |
| Details of High Speed Research Press (HSRP) activation | | | | | | | |
| target maximum activation strain rate (sec$^{-1}$) | 604 | 638 | 604 | 638 | 604 | 638 | 638 |
| HSRP activation pitch (inches) | 0.098" | 0.098" | 0.098" | 0.098" | 0.098" | 0.098" | 0.098" |
| Depth of engagement (DOE) inches | 0.150" | 0.160" | 0.150" | 0.160" | 0.150" | 0.160" | 0.160" |
| Average Strain of activation (%) | 226% | 245% | 226% | 245% | 226% | 245% | 245% |

[1]NW1 = 1 = 15 gsm (70/30 core/sheath, PP/PE) bicomponent spunbond, produced at Fiberweb (Washougal, Washington).
[2]VM blend = Vistamaxx 6102 (92%), Ampacet 10562 (1%), Ampacet 110361 (7%) in weight %. Infuse blend = Infuse 9107 (92%), Ampacet 10562 (1%), Ampacet 110361 (7%) in weight %
[3]Nip gap in controlled compression (CC) is the gap between the two combining rolls and is approximately the thickness of the materials pressed in the opening (~0.005").

TABLE 10

|  | Examples | | | | | | |
|---|---|---|---|---|---|---|---|
|  | 34 | 35 | 36 | 37 | 38 | 39 | 40 |
| NW1[1] | 1 | 1 | 1 | 1 | 1 | 1 | 1 |
| A1: weight % (Infuse 9107/Ampacet 10562/Elite 5800) | 69/1/30 | 69/1/30 | 46/1/53 | 46/1/53 | 24/1/75 | 24/1/75 | 0/1/99 |
| B[2] | VM blend | VM blend | VM blend | VM blend | Infuse blend | VM blend | VM blend |
| A2: weight % (Infuse 9107/Ampacet 10562/Elite 5800) | 69/1/30 | 69/1/30 | 46/1/53 | 46/1/53 | 24/1/75 | 24/1/75 | 0/1/99 |
| NW2[4] | 2 | 2 | 2 | 2 | 2 | 2 | 2 |
| A1 = A2 | yes | yes | yes | yes | yes | yes | yes |
| total film basis weight | 25 gsm | 25 gsm | 25 gsm | 25 gsm | 25 gsm | 25 gsm | 25 gsm |
| film basis weight (gsm) A1/B/A2 | 3/19/3 | 3/19/3 | 3/19/3 | 3/19/3 | 3/19/3 | 3/19/3 | 3/19/3 |
| Melt temperature (° F.) | 422 | 422 | 420 | 420 | 423 | 423 | 417 |
| Line speed (feet per minute) | 314 | 314 | 316 | 316 | 317 | 317 | 322 |
| Nip pressure (psi) or Nip Gap (CC) at combining Rolls[3] | CC | CC | CC | CC | CC | CC | CC |
| Details of On-line High Speed lamination and activation | | | | | | | |
| Interface with Adhesive | A2-NW2 | A2-NW2 | A2-NW2 | A2-NW2 | A2-NW2 | A2-NW2 | A2-NW2 |
| Adhesive type (Bostik) | H2861 | H2861 | H2861 | H2861 | H2861 | H2861 | H2861 |
| Adhesive basis weight (gsm) | 4.5 gsm | 4.5 gsm | 4.5 gsm | 4.5 gsm | 4.5 gsm | 4.5 gsm | 4.5 gsm |
| Nip Gap | 0.005" | 0.005" | 0.005" | 0.005" | 0.005" | 0.005" | 0.005" |
| line speed (m/sec) | 5.33 | 5.33 | 5.33 | 5.33 | 5.33 | 5.33 | 5.33 |
| activation pitch (inches) | 0.100" | 0.100" | 0.100" | 0.100" | 0.100" | 0.100" | 0.100" |
| Depth of engagement (DOE) inches | 0.150" | 0.160" | 0.150" | 0.160" | 0.150" | 0.160" | 0.160" |
| Average Strain of activation (%) | 226% | 245% | 226% | 245% | 226% | 245% | 245% |

[1]NW1 = 1 = 15 gsm (70/30 core/sheath, PP/PE) bicomponent spunbond, produced at Fiberweb (Washougal, Washington).
[2]VM blend = Vistamaxx 6102 (92%), Ampacet 10562 (1%), Ampacet 110361 (7%) in weight %.
[3]Controlled compression (CC) nip gap is the gap between the two combining rolls and is about the thickness of the materials pressed in the opening (~0.005").
[4]NW2 = 2 = 20 gsm (70/30 core/sheath, PP/PE) bicomponent spunbond, produced at Fiberweb (Washougal, Washington).

TABLE 11

|  | Examples | | | | | | |
|---|---|---|---|---|---|---|---|
|  | 27 | 28 | 29 | 30 | 31 | 32 | 33 |
| basis weight (gsm) | 42 | 42 | 39 | 40 | 43 | 42 | 45 |
| Tensile Test Results | | | | | | | |
| Stretch at 1 N/cm (% engineering strain) | 113 | 132 | 121 | 137 | 105 | 122 | 106 |
| Ultimate tensile strength (N/cm) | 3.3 | 3.2 | 2.8 | 2.8 | 3.1 | 2.9 | 3.5 |
| Mode II failure force (N/cm) | na | 2.5 | na | 2.2 | na | 2.6 | 3.1 |

TABLE 12

| | Examples | | | | | | |
|---|---|---|---|---|---|---|---|
| | 34 | 35 | 36 | 37 | 38 | 39 | 40 |
| basis weight (gsm) | — | 64 | — | 61 | — | 64 | 65 |
| 2 Cycle Hysteresis (130% engineering strain) Results (C1 = Cycle 1) | | | | | | | |
| C1 Load force at 100% strain (N/cm) | — | 0.98 | — | 0.84 | — | 0.84 | 1.16 |
| C1 Load force @ 130% strain (N/cm) | — | 1.44 | — | 1.28 | — | 1.24 | 1.68 |
| C1 Unload force at 50% strain (N/cm) | — | 0.15 | — | 0.12 | — | 0.13 | 0.15 |
| C1 Unload force at 30% strain (N/cm) | — | 0.07 | — | 0.06 | — | 0.06 | 0.06 |
| % SET (% strain) | — | 10 | — | 11 | — | 11 | 11 |
| Force Relaxation (%) | — | 36.4 | — | 36.3 | — | 35.1 | 35.8 |
| Tensile Test Results | | | | | | | |
| Basis weight (gsm) | 65 | 65 | 64 | 63 | 64 | 64 | 64 |
| Ultimate tensile strength (N/cm) | 3.9 | 3.7 | 3.9 | 3.5 | 3.8 | 3.3 | 4.3 |
| Strain at break (% engineering strain) | 598 | 353 | 297 | 623 | 494 | 589 | 336 |

Test Methods

Fusion Index

The fusion index is determined by the measurement specified by ASTM D3418-08 "Standard Test Method for Transition Temperatures and Enthalpies of Fusion and Crystallization of Polymers by Differential Scanning Calorimetry." To determine a material's fusion index, the material's enthalpy of fusion, expressed in Joules/gram as measured according to ASTM D3418, shall be divided by 208 J/g. For example, the fusion index of a polypropylene with an experimentally determined enthalpy of fusion of 100 J/g is calculated as $((100/208)*100\%)=48.1\%$. Another example: the fusion index of a PE with an experimentally determined enthalpy of fusion of 30 J/g is calculated as $((30/208)*100\%)=14.4\%$

DSC

Differential Scanning Calorimetry (DSC) measurements are performed according to ASTM D 3418, where DSC samples are prepared by first compression molding a polymer composition into a thin film of around 0.003 inches at about 140° C. between teflon sheets. The film is annealed overnight in a vacuum oven, with vacuum drawn, at a temperature of about 65° C. Samples are punched out of the resulting films using a 6 millimeter diameter skin biopsy punch. The samples are massed to approximately 5-10 milligrams, loaded into small aluminum pans with lids (Perkin Elmer #0219-0041), and crimped using a Perkin Elmer Standard Sample Pan Crimper Press (#0219-0048). Thermal tests and subsequent analyses are performed using a Perkin Elmer DSC 7 equipped with Perkin Elmer Thermal Analyses Software version 4.00.

The melting temperature of a film composition is determined by first heating the DSC sample from about 25° C. to 180° C. at a rate of 20° C. per minute and holding the sample at 180° C. for 3 minutes. The sample is then quenched to minus 60° C. at a rate of 300° C. per minute, held for 3 minutes at minus 60° C., then heated at a rate of 20° C. per minute to 180° C. The melting temperature is taken as the temperature of the melting endotherm's peak. If more than one melting endotherm is present, the endotherm occurring at the highest temperature is used. If no melting peak is present in the second heat but there is one in the first heat (which can happen for film compositions that crystallize very slowly), the sample pan is removed from the DSC, allowed to remain at around 25° C. for 24 hours, reheated in the DSC from about 25° C. to 180° C. at a rate of 20° C. per minute, and then the melting temperature is taken as the highest peak temperature in this third heat.

The rate of crystallization of a film composition at a crystallization temperature of 20 degrees Celsius below its melting temperature is determined by first heating the DSC sample to the desired set temperature (which is above the melting temperature of the film), holding the sample at the set temperature for 2 minutes, and then subjecting the sample to a rapid cooling down to the desired crystallization temperature (about 300° C. per minute). As the temperature is held steady at the crystallization temperature, the crystallization process is evidenced by the appearance of a crystallization exotherm in the DSC isothermal scan as a function of time. A single-point characterization of the crystallization rate consists of reporting the time at which the minimum in the exotherm occurs. The latter is often considered by those skilled in the art as a reasonable indication of the half-time crystallization ($t\frac{1}{2}$) for the material.

One skilled in the art may use this method to determine the crystallization rate of a film sample taken from, for example, a punch taken from an absorbent article component (e.g., an outer cover) comprising an EBL (of course one should take care to first remove any undesired components before making the punch). In this case, additional crystallization peaks may be observed due to the presence of additional components (e.g., nonwoven fibers) but in many cases, these are readily assigned and do not interfere with the crystallization rate determination of the film or film layer of interest.

Blocking Force

All of the steps for this measurement are carried out in a room maintained at a temperature of 23° C.±2° C. and a relative humidity of 50%±5%.

Materials and apparati (all of the following must be located in the same room)

For preparing specimens with edges free from defects, notches, nicks, etc.:
  knife equipped with a sharp #11 Xacto-knife blade or similar
  a steel straight edge is used as a guide for the knife
  office-grade printer/photocopier paper to sandwich material during cutting For conditioning samples
  suitable tray or shelf that allows the samples to be kept reasonably free of contaminants such as dust, aerosols, etc.

For the application of pressure
  laboratory oven set at 46 C (Despach LAC or equivalent) with baffles open.
  suitable weights and flat, rigid plates to apply a compressive pressure of 0.686 MPa to the samples.

For the T-Peel tensile test

MTS Alliance RT/1 or a machine of similar capability, equipped with grips that provide a well-defined area of contact along a single narrow band; and the grips hold the sample along an axis perpendicular to the direction of testing stress, the grips conforming to the description given in ASTM D882.

Strips of an absorbent article component comprising an EBL ("material" for this method) 150 mm×25.4 mm (along the material's machine and transverse directions respectively) are prepared by sandwiching the material between sheets of paper and cutting with a straight-edge and a sharp #11 Xacto-knife blade or similar. Shorter specimens may be used if material availability precludes specimens 150 mm in length.

1. Pre-condition the material at a temperature of 23° C.±2° C. and a relative humidity of 50%±5% for at least 24 hours.
2. Stack 5 samples directly on top of each other with edges aligned such that body-facing nonwoven side on each sample is facing upwards. Each sample in the stack should all be consistently aligned in the MD or CD.
3. Subject one or more stacks of five strips to a compressive load of 0.686 MPa in the lab oven at a temperature of 46° C.±2° C. for 100 hours±1 hour. Leave several millimeters at the end of the strips uncompressed to facilitate subsequent mounting in the tensile tester grips.
4. Remove pressure from specimens.
5. Remove specimens from oven and allow to equilibrate at a temperature of 23° C.±2° C. and a relative humidity of 50%±5% for 45 minutes±15 minutes.
6. Testing one interface at a time, mount the stack in the tensile tester grips in a T-Peel configuration and run crosshead at a speed of 2.12 mm/s (5 inches per minute) for a distance of 100 mm or, in the case of specimens shorter than 150 mm, until the respective pieces separate completely. Use a data acquisition technique that provides a reliable indicator of the maximum force encountered during the peel test.

The maximum force required during the separation of two strips is recorded as the blocking force, reported as Newtons force per cm width of film strip. The average of at least four maximum forces is reported as the material's blocking force. If the strips are so weakly adhered as to separate under their own weight or during mounting, then the blocking force should be taken as zero.

Tensile Test (Mode II) (for Absorbent Article Component Comprising EBL)

This method is used to determine the force versus engineering strain curve of the extrusion bonded laminate. The tensile properties of the materials were measured according to ASTM Method D882-02 with the specifications described below. The measurement is carried out at a constant crosshead speed of 50.8 cm/min at a temperature of 23° C.±2° C. The relationship between the stretch length and the engineering tensile engineering strain $\gamma_{tensile}$ is given by the following equation:

$$\frac{L}{L_o} - 1 = \frac{\gamma_{tensile}}{100} \quad [1]$$

where $L_o$ is the original length, L is the stretched length and $\gamma_{tensile}$ is in units of percent. For example, when a sample with initial gauge length of 5.08 cm is stretched to 10.16 cm, the elongation is 100% engineering strain [((10.16/5.08)−1)*100=100% engineering strain] and when a sample with initial gauge length of 5.08 cm is stretched to 35.6 cm, the elongation is 600% engineering strain [((35.6/5.08)−1)*100=600% engineering strain]. The material to be tested is cut into a substantially rectilinear shape. Sample dimensions are selected to achieve the required engineering strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 25.4 mm wide by approximately 100 mm long. Shorter specimens may be used, however, if material availability precludes specimens 100 mm in length. (within the limitations outlined below).

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are wider than the elastic member. Typically 2.00 inch (5.08 cm) wide grips are used. The grips are air actuated grips designed to concentrate the entire gripping force along an area of contact; and the grips hold the sample along an axis perpendicular to the direction of testing stress, the grip face set in the upper and lower grips having one flat surface and an opposing face with a 6 mm line contact (half round protrusion) to minimize slippage of the sample. The load cell is selected so that the forces measured will be between 10% and 90% of the capacity of the load cell or the force range used. Typically a 100 N load cell is used. The fixtures and grips are installed. The instrument is calibrated according to the manufacturer's instructions. The distance from the center of the half round of the upper grip face to the center of the half round of the lower grip face (gauge length) is 2.00 inches (50.8 mm), which is measured with a steel ruler held beside the grips. The force reading on the instrument is zeroed to account for the mass of the fixture and grips. The instrument is located in a temperature-controlled room for measurements performed at 23° C.±2° C. The sample is equilibrated a minimum of 1 hour at 23° C.±2° C. before testing. The mass and dimensions of the specimen are measured before testing and are used to calculate the basis weight of the specimen in grams per square meter (gsm). The specimen is mounted into the grips in a manner such that the longitudinal axis of the sample is substantially parallel to the gauge length direction, there is no slack and the force measured is approximately 0.01N. The sample is deformed at a constant crosshead speed of 20 inches/min. (50.8 cm/min) to about 1000% engineering strain or until the sample breaks or exhibits a more than nominal loss of mechanical integrity. The force, time and displacement are measured during the tensile test at a data acquisition frequency of 50 Hz. A minimum of three samples is used to determine the average test values. For different sample dimensions, the crosshead speed is adjusted to maintain the appropriate engineering strain rate for the test. For example, a crosshead speed of 10 inches/min (25.4 cm/min) would be used for a sample gauge length of 1.00 inch (25.4 mm).

For extrusion bonded laminates that exhibit a yield drop, such as shown in FIG. 4, the yield point identifies the % engineering strain after which the force decreases (or does not increase) with increasing elongation, and is usually caused by localized breaking of the nonwoven fibers and/or the onset of delamination of the nonwoven fibers from the elastomeric film. The post yield force region may reach a minimum or plateau. In some examples, the post yield force plateau region is followed by the sample breaking (see for example, FIG. 5B). In other examples the post yield force plateau region is followed by an increase in force with increasing elongation and ultimately the sample breaks (see for example, FIG. 5A). The post yield plateau force region of the extrusion bonded laminate tensile curve is used to measure the Mode II (sliding or in-plane shear mode) failure force; and the post yield plateau force region of the extrusion bonded laminate tensile curve is used as an indicator of the extrusion laminate bond strength. The Mode II failure force is reported in N/cm and is the average force in the post yield minimum or plateau force region, the region being selected such that the percent relative standard deviation of the average (% RSD) is less than 10%. The Mode II failure is described by Richard W. Hertzberg in Deformation and Fracture Mechanics of Engineering Materials, $2^{nd}$ edition, John Wiley & Sons, New York (1976, 1983), page 276.

The tensile test results are reported for each example as one or a combination of the following properties; the percent engineering strain at 1 N/cm force (the elongation at 1 N/cm), the Mode II failure force in N/cm, the percent engineering strain at break, and the ultimate tensile strength in N/cm (i.e., the peak force divided by the sample width, for example, at the "break" in FIG. 5A and at the "yield point" in FIG. 5B,). A minimum of three samples is used to determine the average test values.

Typical Mode II failure values for well bonded laminates used in absorbent articles of the present invention are from about 1.1 N/cm to about 3.5 N/cm for activated samples.

In some cases, it may not be possible to measure the Mode II failure force of the laminate, for example in cases where the sample breaks before the Mode II failure starts. If it is not possible to measure the Mode II failure force, the laminate bond strength can be measured by the Tensile Test (Mode I) as follows:

Tensile Test (Mode I)

The Mode I T-peel tensile test method is performed at room temperature (23° C.±2° C.). The material to be tested is cut into a substantially rectilinear shape. Sample dimensions are to be selected to achieve the required strain with forces appropriate for the instrument. Suitable sample dimensions are approximately 25.4 mm wide by approximately 100 mm long. Shorter specimens may be used, however, if material availability precludes specimens 100 mm in length. The length of the sample is the direction perpendicular to the axis of stretch. Suitable instruments, grips, grip faces, software for data acquisition, calculations, reports, and definition of percent strain are described in the Tensile Test (Mode II) method section above.

The load cell is selected so that the forces measured fall between 10% and 90% of the capacity of the load cell or the force range used. Typically a 25 N load cell is used. The fixtures and grips are installed. The instrument is calibrated according to the manufacturer's instructions. The distance between the lines of gripping force (gauge length as described in Tensile Test-Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before sample preparation for the T-peel test and are used to calculate the basis weight of the specimen in grams per square meter (gsm). The samples (approximately 25.4 mm wide by approximately 100 mm long) are prepared for T-peel test using the following procedure: (1) Mark the sample with a pen, making a line across the 2.54 cm width of the sample at a location 2.54 cm from the end of the sample. (2) Stretch the sample in small increments in the 6.45 cm$^2$ area between the pen mark and the end of the sample to initiate delamination of the nonwoven fibers from the film. (3) Secure a piece of masking tape (Corporate Express, MFG#CEB1X60TN, from Paperworks, Inc at pwi-inc.com or equivalent), 5.08 cm long and 2.54 cm wide, centered across the top 2.54 cm width of sample on the end of the sample which has been stretched to initiated delamination, Apply pressure to bond the tape to the sample. In the case of a bi-laminate, the tape is placed on the film surface. In the case of a tri-laminate, the tape is placed on the 2.54 cm wide surface opposite to the side for which the laminate bond strength is to be measured. This tape will support the film portion of the t-peel sample after steps 4 and 5 are complete. (4) Carefully pull the fibers off of the film on the side of the sample that does not have tape, in the 6.45 cm$^2$ area between the pen mark and the end of the sample. For samples that are well bonded, this can be achieved by gently abrading the sample with a rubber eraser in the approximate direction toward the pen mark. (5) Carefully peel the nonwoven off of the film to the pen mark. (6) Place a second piece of tape, 5.08 cm long and 2.54 cm wide, centered across the top 2.54 cm width of the nonwoven fibers that have been intentionally delaminated from the sample to form the nonwoven portion of the T-peel sample. A minimum of five samples is used to determine the average test value. To perform the T-peel test, mount the sample into the grips in a T-peel configuration with the nonwoven portion of the T-peel sample mounted in the upper grip and the film portion of the T-peel sample mounted into the bottom grip. The specimen is mounted into the grips in a manner such that there is minimal slack and the force measured is less than about 0.02N. The crosshead moves up at a constant crosshead speed of 30.5 cm/min and the sample is peeled until the respective materials (nonwoven fibers and film) separate completely. The force and extension data are acquired at a rate of 50 Hz during the peel. The peak force (N/cm) during the first 50 mm of extension is reported as the Mode I peel force. Typical Mode I peel values for a well bonded laminate used in absorbent articles of the present invention are from about 1.0 N/cm to about 2.5 N/cm for non-activated samples and from about 0.5 N/cm to about 2.0 N/cm for activated samples.

Two Cycle Hysteresis Test

This method is used to determine properties that may correlate with the forces experienced by the consumer during application of the product containing the extrusion bonded laminate and how the product fits once it is applied.

The two cycle hysteresis test method is performed at room temperature (23° C.±2° C.). The material to be tested is cut into a substantially rectilinear shape. Sample dimensions are selected to achieve the required strain with forces appropriate for the instrument. Suitable sample dimensions are approximately 25.4 mm wide by approximately 76.2 mm long. Shorter specimens may be used, however, if material availability precludes specimens 76.2 mm in length. The sample is selected and mounted such that the direction of elongation in the test method is perpendicular to the width of the sample, such that it can be elongated to a length of at least the maximum percent strain of the hysteresis test. Suitable instruments, grips, grip faces, software for data acquisition, calculations and reports and definition of percent strain are described in the Tensile Test (Mode II) method section above.

The load cell is selected so that the forces measured fall between 10% and 90% of the capacity of the load cell or the force range used. Typically a 25 N or 100N load cell is used. The fixtures and grips are installed. The instrument is calibrated according to the manufacturer's instructions. The distance between the line of gripping force (gauge length, as described in the Tensile test-Mode II) is 2.54 cm, which is measured with a steel ruler held beside the grips. The force reading on the instrument is zeroed to account for the mass of the fixture and grips. The samples are equilibrated at 23° C.±2° C. for a minimum of one hour before testing. The mass, length and width of the specimen are measured before testing and are used to calculate the basis weight of the specimen in grams per square meter (gsm). A minimum of five samples is used to determine the average test values. The specimen is mounted into the grips in a manner such that there is minimal slack and the force measured is less than 0.02N. The first segment of the two cycle hysteresis test method is a gauge adjustment step using a 5 gram preload slack adjustment. The engineering tensile engineering strain $\gamma_{tensile}$ is defined in the Tensile Test Method section above and with a slack adjustment preload segment, $L_o$ is the adjusted gauge length, L is the stretched length and $\gamma_{tensile}$ is in units of percent. The Two Cycle Hysteresis Test is done using the following segments:

(1) Slack adjustment: Move the crosshead at 13 mm/min. until the specified 5 gf slack adjustment preload is achieved. The distance between the lines of gripping force at the 5 gf slack adjustment preload is the adjusted gauge length.

(2) Move the crosshead to achieve the specified percent engineering strain (i.e., engineering strain=130%) at a constant crosshead speed of 254 mm/min. For example, if the adjusted gauge length from segment 1 is 26.00 mm, the sample is stretched to 59.80 mm and the % engineering strain=((59.80/26.00)−1)*100=130%.

(3) Hold the sample for 30 seconds at the specified percent engineering strain (i.e., engineering strain=130%).

(4) Reduce engineering strain to 0% engineering strain (i.e., return grips to adjusted gauge length) at a constant crosshead speed of 254 mm/min.

(5) Hold the sample for 60 seconds at 0% engineering strain. (segments 1 to 5 complete Cycle 1)

(6) Repeat segments 2 through 5 to complete the second cycle of the Two Cycle Hysteresis Test.

The method reports Cycle 1 load forces at 100% engineering strain and 130% engineering strain (from segment 2), Cycle 1 unload force at 50% engineering strain and 30% engineering strain (from segment 4), percent set and force relaxation. The forces are reported in N/cm, where cm is the width of the sample. The percent set is defined as the percent engineering strain after the start of the second load cycle (from segment 6) where a force of 7 grams is measured (percent set load=7 grams). Force relaxation is the reduction in force during the hold in segment 3 and is reported as a percent. Percent force relaxation is calculated from the forces measured at 130% engineering strain during Cycle 1 and is equal to 100*[((initial force at 130% engineering strain)−(force at 130% engineering strain after the 30 second hold))/(initial force at 130% engineering strain)].

For different sample dimensions, the crosshead speed is adjusted to maintain the appropriate strain rate for each portion of the test. For example; a crosshead speed of 127 mm/min would be used in segments 2, 4 and 6 for a sample gauge length of 12.7 mm and a crosshead speed of 381 mm/min would be used in segments 2, 4 and 6 for a sample gauge length of 38.1 mm. Additionally, for samples with different widths, the slack preload force (5 grams per 2.54 cm width=1.97 g/cm) and the percent set load force (7 grams per 2.54 cm width=2.76 g/cm) must be adjusted for the different sample width. The Two Cycle Hysteresis Test may also be modified depending on the expected properties of the material tested. For example, if the sample is not capable of being elongated to 130% engineering strain without breaking, the sample is to be elongated to 100% engineering strain. And, if the sample is not capable of being elongated to 100% engineering strain, the sample is to be elongated to 70% engineering strain. In the latter two cases (elongation to 100% or 70% strain), force relaxation is determined at the maximum elongation of Cycle 1 as defined above for elongation of 130% engineering strain.

Permanent Set

See the Two Cycle Hysteresis Test immediately above.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a topsheet;
an outer cover;
an absorbent core disposed between the topsheet and outer cover;
wherein the outer cover comprises an extrusion bonded laminate, the extrusion bonded laminate comprising:
a multi-layer coextruded elastomeric film, comprising a core layer, a first outer layer, and a second outer layer, wherein the core layer is between the first and second outer layers;
a nonwoven consisting of fibers and/or filaments;
wherein the first outer layer is non-adhesively joined to the nonwoven via extrusion coating, such that the first outer layer is a tie layer between the core layer and the nonwoven;
wherein the second outer layer is non-adhesively joined to the core layer, such that the second outer layer is a skin layer;
wherein the first and second outer layers comprise polyolefin elastomers (POEs);
wherein the first and second outer layers comprise a blend of two ethylene-rich copolymers, wherein ethylene is between 10% and 97%
wherein the extrusion bonded laminate is mechanically activated using intermeshing gears;
wherein the outer cover is elastic to at least 50% engineering strain;
wherein the nonwoven has a high chemical affinity for the first outer layer;
wherein the first outer layer has a low chemical affinity for the core layer; and
wherein the first outer layer comprises an amount of draw down polymer greater than 45 wt%.

2. The absorbent article of claim 1, wherein the first and second outer layers have a fusion index from about 10% to about 40%.

3. The absorbent article of claim 1, wherein the nonwoven comprises bicomponent fibers, the fibers comprising a core and a sheath.

4. The absorbent article of claim 3, wherein the sheath comprises polyethylene and the core comprises polypropylene.

5. The absorbent article of claim 4, wherein the laminate bond strength is from about 2.2 to about 3.5 N/cm, as measured by the Tensile Test (Mode II).

6. The absorbent article of claim 3, wherein the first outer layer comprises at least 45% of a polymer comprising more than 10 w% ethylene.

7. The absorbent article of claim 1, wherein the core of the elastomeric film is selected from the group consisting of an ethylene copolymer having a fusion index from about 5% to about 20%, a propylene copolymer having a fusion index from about 5% to about 20%, and combinations thereof.

8. The absorbent article of claim 1, wherein the multi-layer coextruded elastomeric film has a basis weight from about 20 gsm to about 30 gsm.

9. The absorbent article of claim 1, wherein the extrusion bonded laminate further comprises an adhesive.

10. The absorbent article of claim 1, wherein the nonwoven comprises fibers that are not round in cross section.

11. The absorbent article of claim 1, further comprising a second nonwoven joined to the second outer layer.

12. The absorbent article of claim 1, wherein an exterior surface of the second outer layer has a blocking force from 0.07 to 0.4 N/cm.

13. The absorbent article of claim 1, wherein the extrusion bonded laminate is adhesive free.

14. The absorbent article of claim 1, wherein the elastomeric film comprises at least 50%, by weight, of a polyolefinic elastomer.

15. The absorbent article of claim 1, wherein the elastomeric film comprises:
   at least one olefin-based elastomeric polymer; and
   at least one draw down polymer;
   wherein the elastomeric film has a permanent set of no more than 15% as measured by the Two-Cycle Hysteresis Test Method using 100% maximum engineering strain.

16. The absorbent article of claim 1, wherein the first and second outer layers are compositionally identical.

17. The absorbent article of claim 1, wherein the outer cover has an ultimate tensile strength from 3 N/cm to 5.3 N/cm.

18. An absorbent article comprising:
   a topsheet;
   an outer cover;
   an absorbent core disposed between the topsheet and outer cover;
   wherein the outer cover comprises an extrusion bonded laminate, the extrusion bonded laminate comprising:
      a multi-layer coextruded elastomeric film, comprising a core layer, a first outer layer, and a second outer layer, wherein the core layer is between the first and second outer layers;
      a nonwoven consisting of fibers and/or filaments;
      wherein the first outer layer is non-adhesively joined to the nonwoven via extrusion coating such that the first outer layer is a tie layer between the core layer and the nonwoven;
      wherein the second outer layer is non-adhesively joined to the core layer, such that the second outer layer is a skin layer;
      wherein the first and second outer layers comprise polyolefin elastomers (POEs);
      wherein the first and second outer layers comprise a blend of two ethylene-rich copolymers, wherein ethylene is between 10% and 97%
      wherein the extrusion bonded laminate is mechanically activated using intermeshing gears;
   wherein the outer cover is elastic to at least 50% engineering strain;
   wherein the nonwoven has a high chemical affinity for the first outer layer;
   wherein the first outer layer has a low chemical affinity for the core layer;
   wherein the first outer layer comprises an amount of draw down polymer greater than 75 wt% ; and
   wherein the multi-layer coextruded elastomeric film has a basis weight from 1 gsm to 25 gsm.

* * * * *